US011724007B2

(12) United States Patent
Cichocki et al.

(10) Patent No.: US 11,724,007 B2
(45) Date of Patent: Aug. 15, 2023

(54) OPERATING ROOM COATING APPLICATOR AND METHOD

(71) Applicant: Ethicon, Inc., Somerville, NJ (US)

(72) Inventors: Frank Richard Cichocki, Easton, PA (US); Robert J. Tannhauser, Bridgewater, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 295 days.

(21) Appl. No.: 16/697,228

(22) Filed: Nov. 27, 2019

(65) Prior Publication Data

US 2020/0171520 A1 Jun. 4, 2020

Related U.S. Application Data

(60) Provisional application No. 62/773,102, filed on Nov. 29, 2018.

(51) Int. Cl.
*A61L 27/54* (2006.01)
*A61L 2/03* (2006.01)
(Continued)

(52) U.S. Cl.
CPC ................. *A61L 27/54* (2013.01); *A61L 2/03* (2013.01); *A61L 2/07* (2013.01); *A61L 2/20* (2013.01); *A61L 2/26* (2013.01); *A61L 17/005* (2013.01); *A61L 17/145* (2013.01); *A61L 31/10* (2013.01); *A61L 31/14* (2013.01); *A61L 31/16* (2013.01); *B05B 7/1606* (2013.01);
(Continued)

(58) Field of Classification Search
CPC ...... B05B 7/1606; B05B 12/081; A61L 27/04
See application file for complete search history.

(56) References Cited

U.S. PATENT DOCUMENTS 3,976,049 A 8/1976 Yamashita
4,057,047 A 11/1977 Gossett
(Continued)

FOREIGN PATENT DOCUMENTS

CN 1827178 A 9/2006
CN 101553359 A * 10/2009 ............. C23C 24/00
(Continued)

OTHER PUBLICATIONS

International Search Report dated Feb. 27, 2020 for Application No. PCT/IB2019/060229.
(Continued)

*Primary Examiner* — Cachet I Proctor

(57) ABSTRACT

A disposable coating applicator container for applying a coating of a therapeutic agent upon an object to be coated. The disposable coating applicator container includes a sealable container, the sealable container having a container bottom, the container bottom having upwardly extending walls, each upwardly extending wall terminating in an upper edge, and a closure for sealing a device compartment formed in part by the upwardly extending walls, the closure adjacent to the upper edges of the upwardly extending walls; and a therapeutic agent positioned in fluid communication with the device compartment, wherein the disposable coating applicator container comprises a flexible material and is in the form of a bag-like structure.

33 Claims, 11 Drawing Sheets

(51) Int. Cl.

| | |
|---|---|
| ***A61L 2/07*** | (2006.01) |
| ***A61L 2/20*** | (2006.01) |
| ***A61L 2/26*** | (2006.01) |
| ***A61L 17/00*** | (2006.01) |
| ***B05B 7/16*** | (2006.01) |
| ***B05B 15/00*** | (2018.01) |
| ***A61L 17/14*** | (2006.01) |
| ***C09D 7/20*** | (2018.01) |
| ***C09D 7/62*** | (2018.01) |
| ***A61L 31/10*** | (2006.01) |
| ***A61L 31/14*** | (2006.01) |
| ***A61L 31/16*** | (2006.01) |
| ***C09D 5/14*** | (2006.01) |
| ***C09D 183/04*** | (2006.01) |
| ***C10M 107/50*** | (2006.01) |
| ***B05B 12/08*** | (2006.01) |
| ***B05B 17/06*** | (2006.01) |
| ***B05D 1/02*** | (2006.01) |
| ***B05D 3/04*** | (2006.01) |
| *C10N 40/00* | (2006.01) |
| *C10N 30/16* | (2006.01) |
| *C10N 50/08* | (2006.01) |
| *A61M 11/00* | (2006.01) |

(52) U.S. Cl.

CPC .......... *B05B 7/1686* (2013.01); *B05B 12/081* (2013.01); *B05B 15/00* (2013.01); *B05B 17/0615* (2013.01); *B05D 1/02* (2013.01); *B05D 3/0493* (2013.01); *C09D 5/14* (2013.01); *C09D 7/20* (2018.01); *C09D 7/62* (2018.01); *C09D 183/04* (2013.01); *C10M 107/50* (2013.01); *A61L 2202/181* (2013.01); *A61L 2202/182* (2013.01); *A61L 2300/202* (2013.01); *A61L 2300/404* (2013.01); *A61L 2300/606* (2013.01); *A61L 2400/10* (2013.01); *A61L 2420/02* (2013.01); *A61L 2420/04* (2013.01); *A61L 2420/06* (2013.01); *A61M 11/005* (2013.01); *C10M 2229/0445* (2013.01); *C10N 2030/16* (2013.01); *C10N 2040/50* (2020.05); *C10N 2050/08* (2013.01)

(56) References Cited

U.S. PATENT DOCUMENTS

| | | | | |
|---|---|---|---|---|
| 4,940,542 | A * | 7/1990 | Simizu | B65D 83/32 210/321.89 |
| 5,046,479 | A | 9/1991 | Usui | |
| 5,205,277 | A | 4/1993 | Chao-tsung | |
| 5,474,797 | A | 12/1995 | Sioshansi et al. | |
| 6,143,370 | A * | 11/2000 | Panagiotou | A61L 31/10 427/422 |
| 8,315,700 | B2 | 11/2012 | Citron et al. | |
| 8,551,555 | B2 | 10/2013 | Burghard et al. | |
| 8,790,677 | B2 | 7/2014 | Mckay | |
| 8,997,978 | B2 | 4/2015 | Stopek | |
| 9,220,294 | B2 * | 12/2015 | McCullough | A24B 13/00 |
| 9,364,215 | B2 | 6/2016 | Stopek | |
| 9,688,459 | B2 * | 6/2017 | Stanley | B05B 11/00412 |
| 9,848,955 | B2 | 12/2017 | Buevich | |
| 9,987,400 | B1 | 6/2018 | Chen | |
| 10,314,951 | B2 | 6/2019 | Chen | |
| 2002/0022762 | A1 * | 2/2002 | Beane | A61B 1/127 600/101 |
| 2004/0068294 | A1 | 4/2004 | Scalzo | |
| 2004/0220614 | A1 * | 11/2004 | Scalzo | A61B 17/06114 606/228 |
| 2005/0034723 | A1 * | 2/2005 | Bennett | A61K 9/007 128/203.12 |
| 2005/0181116 | A1 | 8/2005 | Worsham | |
| 2005/0188921 | A1 * | 9/2005 | Malone | A61L 29/16 118/715 |
| 2007/0092494 | A1 * | 4/2007 | Higgins | A61K 35/36 424/93.7 |
| 2007/0218197 | A1 | 9/2007 | Kurono | |
| 2007/0254091 | A1 | 11/2007 | Fredrickson et al. | |
| 2007/0292305 | A1 * | 12/2007 | Dempsey | A61L 2/206 422/33 |
| 2009/0099532 | A1 | 4/2009 | Cuevas | |
| 2009/0169714 | A1 | 7/2009 | Burghard et al. | |
| 2010/0021620 | A1 * | 1/2010 | Coates | C23C 14/12 427/2.24 |
| 2010/0163435 | A1 | 7/2010 | Fischer | |
| 2011/0114744 | A1 * | 5/2011 | Ricciardi | A61L 2/22 239/4 |
| 2013/0264226 | A1 | 10/2013 | Prikril et al. | |
| 2018/0193537 | A1 | 7/2018 | Honglei | |
| 2018/0272136 | A1 | 9/2018 | Horn | |
| 2019/0125938 | A1 | 5/2019 | Chen | |
| 2020/0345885 | A1 | 11/2020 | Lewis | |

FOREIGN PATENT DOCUMENTS

| | | | | | |
|---|---|---|---|---|---|
| CN | 101553359 | A | | 10/2009 | |
| CN | 101909666 | A | | 12/2010 | |
| CN | 102026589 | A | | 4/2011 | |
| CN | 102423266 | A | | 4/2012 | |
| CN | 103083730 | A | | 5/2013 | |
| CN | 203647752 | U | * | 6/2014 | |
| CN | 104203125 | A | | 12/2014 | |
| CN | 106730044 | A | | 5/2017 | |
| CN | 107454835 | A | | 12/2017 | |
| EP | 0761243 | A1 | | 3/1997 | |
| EP | 1510558 | A1 | | 3/2005 | |
| EP | 2833799 | A1 | | 2/2015 | |
| EP | 2833799 | B1 | * | 8/2017 | A61B 17/06133 |
| WO | 1993/07924 | A1 | | 4/1993 | |
| WO | 2004032704 | A2 | | 4/2004 | |
| WO | 2004037443 | A1 | | 5/2004 | |
| WO | 2009046093 | A2 | | 4/2009 | |
| WO | 2017218832 | A1 | | 12/2017 | |

OTHER PUBLICATIONS

International Search Report dated Feb. 27, 2020 for Application No. PCT/IB2019/060231.

International Search Report dated Feb. 27, 2020 for Application No. PCT/IB2019/060232.

* cited by examiner

OPERATING ROOM COATING APPLICATOR AND METHOD

CROSS-REFERENCE TO RELATED APPLICATIONS

This application claims the benefit of U.S. Provisional Application No. 62/773,102 filed Nov. 29, 2018, the contents of which are herein incorporated by reference in their entirety for all purposes.

This application is related to U.S. Non-Provisional application Ser. No. 16/697,225, and to U.S. Non-Provisional application Ser. No. 16/697,227, being filed concurrently herewith and having a common assignee, the contents of each are herein incorporated by reference in their entirety for all purposes.

FIELD

The present disclosure relates generally to apparatus and methods for coating objects with a therapeutic agent, and more particularly, to apparatus and methods suitable for use in an operating room to coat surgical instruments or surgical implants with a therapeutic agent in the course of conducting surgery, with minimal interruption and delay.

ENVIRONMENT

Each year, about twenty-seven million surgical procedures are performed in the United States. Post-operative or surgical site infections ("SSIs") occur in approximately two to three percent of all cases. This rate corresponds with the occurrence of more than 675,000 SSIs each year.

The occurrence of SSIs is often associated with bacteria that can colonize on implantable medical devices used in surgery. During a surgical procedure, bacteria from the surrounding atmosphere may enter the surgical site and attach to the medical device. Specifically, bacteria can spread by using the implanted medical device as a pathway to surrounding tissue. Such bacterial colonization on the medical device may lead to infection and trauma to the patient. Accordingly, SSIs may significantly increase the cost of treatment to patients.

Implantable medical devices that contain antimicrobial agents applied to or incorporated therein have been disclosed and/or exemplified in the art. Examples of such devices are disclosed in European Patent Application No. EP 0 761 243. Actual devices exemplified in the application include French Percuflex catheters. The catheters were dip-coated in a coating bath containing 2,4,4'-tricloro-2-hydroxydiphenyl ether (Ciba Geigy Irgasan (DP300)) and other additives. The catheters then were sterilized with ethylene oxide and stored for thirty days. Catheters coated with such solutions exhibited antimicrobial properties, i.e., they produced a zone of inhibition when placed in a growth medium and challenged with microorganism, for thirty days after being coated.

US Published Patent Application 2004/0220614 to Scalzo, et. al., incorporated herein by reference in its entirety, describes an antimicrobial suture assembly comprising a containment compartment comprising one or more surfaces having an antimicrobial agent disposed thereon, said antimicrobial agent being selected from the group consisting of halogenated hydroxyl ethers, acyloxydiphenyl ethers, and combinations thereof, in an amount sufficient to substantially inhibit bacterial colonization on said containment compartment; and a suture positioned within the containment compartment, the suture comprising one or more surfaces having an antimicrobial agent disposed thereon, said antimicrobial agent being selected from the group consisting of halogenated hydroxyl ethers, acyloxydiphenyl ethers, and combinations thereof, and at least one active agent selected from the group consisting of a biocide, a disinfectant, an antiseptic, an antibiotic, an antimicrobial peptide, a lytic bacteriophage, a surfactant; an adhesion blocker; an oligonucleotide, an efflux pump inhibitors; a photosensitive dye, an immune modulator and a chelator.

SUMMARY

In one aspect, provided is a disposable coating applicator container for applying a coating of a therapeutic agent upon an object to be coated. The disposable coating applicator container includes a sealable container, the sealable container having a container bottom, the container bottom having upwardly extending walls, each upwardly extending wall terminating in an upper edge, and a closure for sealing a device compartment formed in part by the upwardly extending walls, the closure adjacent to the upper edges of the upwardly extending walls; and a therapeutic agent positioned in fluid communication with the device compartment, wherein the disposable coating applicator container comprises a flexible material and is in the form of a bag-like structure.

In some forms, the therapeutic agent is entrained in a carrier.

In some forms, the therapeutic agent comprises triclosan and the carrier comprises a sheet, pad or film comprising an absorbable polymer or silicone.

In some forms, the absorbable polymer is lactide glycolide copolymer.

In some forms, the disposable coating applicator container also includes a heat source for vaporizing the therapeutic agent and causing the therapeutic agent to flow into the device compartment and coat the object.

In some forms, the heat source is a resistance heater.

In some forms, the carrier is positioned adjacent the resistance heater.

In some forms, the resistance heater is located within the disposable coating applicator container.

In some forms, the resistance heater is located within the device compartment.

In some forms, the resistance heater is located outside the disposable coating applicator container.

In some forms, the disposable coating applicator container also includes a power supply for powering the resistance heater.

In some forms, the power supply is located within the disposable coating applicator container.

In some forms, the power supply is a battery.

In some forms, the heat source is a chemical heat pack.

In some forms, the disposable coating applicator container includes a vapor circulating pump, the vapor circulating pump in fluid communication with the heated therapeutic agent entrained in the carrier.

In some forms, the disposable coating applicator container includes a gas circulating pump, the gas circulating pump in fluid communication with the device compartment.

In some forms, the vapor circulating pump and the gas circulating pump are hand-operated, bulb- or bellows-type pumps.

In some forms, the disposable coating applicator container includes a recirculating pump, the recirculating pump in fluid communication with the heated therapeutic agent entrained in the carrier and the device compartment, and is configured to alternately apply pressure and vacuum via a check-valve system.

In some forms, the disposable coating applicator container includes a therapeutic agent supply cannula, in fluid communication with a first side of the device compartment and an intake cannula in fluid communication with a second side of the device compartment.

In some forms, the therapeutic agent supply cannula and the intake cannula each have a plurality of apertures spaced thereabout to more evenly provide the therapeutic agent and more evenly draw return intake gas.

In some forms, the disposable coating applicator container includes a recirculating fan, powered by the power supply, to facilitate the provision of therapeutic agent and the return of intake gas.

In some forms, the disposable coating applicator container includes a microprocessor for controlling the recirculating fan.

In some forms, the disposable coating applicator container includes an external power block, the external power block having a slit for positioning the disposable coating applicator container therein, and applying heat to the therapeutic agent entrained within the carrier.

In some forms, the therapeutic agent comprises a fluid and the disposable coating applicator container further comprises an atomizer operable to atomize the therapeutic agent.

In some forms, the atomizer comprises a nebulizer.

In some forms, the atomizer comprises an ultrasonic nebulizer and/or a jet nebulizer and/or a vibrating mesh nebulizer and/or a pressurized spray nozzle nebulizer and/or a vibrated frit nebulizer and/or a thermally driven, wick-based aerosol generator and/or a heated capillary aerosol generator and/or a vaporizer.

In some forms, the therapeutic agent comprises a suspension and/or an emulsion and/or a solution.

In some forms, a source of vacuum is applied to the device compartment.

In some forms, the heat source is an external induction or hot water heat source.

In some forms, the heat source is a metallic element positioned adjacent the therapeutic agent.

In some forms, the heat source comprises an external source of energy.

In some forms, the heat source comprises a system employing microwave or radiofrequency energy.

In some forms, the object is a surgical implant and/or a medical device.

In some forms, the flexible material comprises a polymer, copolymer or blends thereof.

In another aspect, provided is a method of coating an object with a therapeutic agent. The method includes the steps of placing an object to be coated into a disposable coating applicator container, the disposable coating applicator container comprising: a sealable container, the sealable container having a container bottom, the container bottom having upwardly extending walls, each upwardly extending wall terminating in an upper edge, and a closure for sealing a device compartment formed in part by the upwardly extending walls, the closure adjacent to the upper edges of the upwardly extending walls; and a therapeutic agent positioned in fluid communication with the device compartment; sealing the device compartment; dispersing a therapeutic agent within the sealed device compartment by atomizing the therapeutic agent; and coating the object with the therapeutic agent, wherein the disposable coating applicator container comprises a flexible material and is in the form of a bag-like structure.

In some forms, the method includes the step of removing the coated object from the device compartment.

In some forms, the therapeutic agent is entrained in a carrier.

In some forms, the therapeutic agent comprises triclosan and the carrier comprises a sheet, pad or film comprising an absorbable polymer or silicone.

In some forms, the absorbable polymer is lactide glycolide copolymer.

In some forms, the disposable coating applicator container further comprises a heat source for vaporizing the therapeutic agent and causing the therapeutic agent to flow into the device compartment and coat the object.

In some forms, the heat source is a resistance heater.

In some forms, the carrier is positioned adjacent the resistance heater.

In some forms, the resistance heater is located within the disposable coating applicator container.

In some forms, the resistance heater is located within the device compartment.

In some forms, the resistance heater is located outside the disposable coating applicator container.

In some forms, the disposable coating applicator container further comprises a power supply for powering the resistance heater.

In some forms, the power supply is located within the disposable coating applicator container.

In some forms, the power supply is a battery.

In some forms, the heat source is a chemical heat pack.

In some forms, the disposable coating applicator container further comprises a vapor circulating pump, the vapor circulating pump in fluid communication with the heated therapeutic agent entrained in the carrier.

In some forms, the disposable coating applicator container further comprises a gas circulating pump, the gas circulating pump in fluid communication with the device compartment.

In some forms, the vapor circulating pump and the gas circulating pump are hand-operated, bulb- or bellows-type pumps.

In some forms, the disposable coating applicator container further comprises a recirculating pump, the recirculating pump in fluid communication with the heated therapeutic agent entrained in the carrier and the device compartment, and is configured to alternately apply pressure and vacuum via a check-valve system.

In some forms, the disposable coating applicator container further comprises a therapeutic agent supply cannula, in fluid communication with a first side of the device compartment and an intake cannula in fluid communication with a second side of the device compartment.

In some forms, the therapeutic agent supply cannula and the intake cannula each have a plurality of apertures spaced thereabout to more evenly provide the therapeutic agent and more evenly draw return intake gas.

In some forms, the disposable coating applicator container further comprises a recirculating fan, powered by the power supply, to facilitate the provision of therapeutic agent and the return of intake gas.

In some forms, the disposable coating applicator container further comprises a microprocessor for controlling the recirculating fan.

In some forms, the disposable coating applicator container further comprises an external power block, the external power block having a slit for positioning the disposable coating applicator container therein, and applying heat to the therapeutic agent entrained within the carrier.

In some forms, the therapeutic agent comprises a fluid and the disposable coating applicator container further comprises an atomizer operable to atomize the therapeutic agent.

In some forms, the atomizer comprises a nebulizer.

In some forms, the atomizer comprises an ultrasonic nebulizer and/or a jet nebulizer and/or a vibrating mesh nebulizer and/or a pressurized spray nozzle nebulizer and/or a vibrated frit nebulizer and/or a thermally driven, wick-based aerosol generator and/or a heated capillary aerosol generator and/or a vaporizer.

In some forms, the therapeutic agent comprises a suspension and/or an emulsion and/or a solution.

In some forms, a source of vacuum is applied to the device compartment.

In some forms, the heat source is an external induction or hot water heat source.

In some forms, the heat source is a metallic element positioned adjacent the therapeutic agent.

In some forms, the heat source comprises an external source of energy.

In some forms, the object is a surgical implant and/or a medical device.

In some forms, the flexible material comprises a polymer, copolymer or blends thereof.

Additionally, the method can further comprise contacting the medical device with the vaporized therapeutic agent while the vaporized therapeutic agent is in a heated condition. During the contacting, the temperature of the medical device increases by less than 15° C.

BRIEF DESCRIPTION OF THE DRAWINGS

The embodiments shown in the figures and subsequently described herein are presented by way of example, and not by way of limitation. In the figures, like reference numerals refer to similar elements; and wherein.

DETAILED DESCRIPTION

Figure 1:
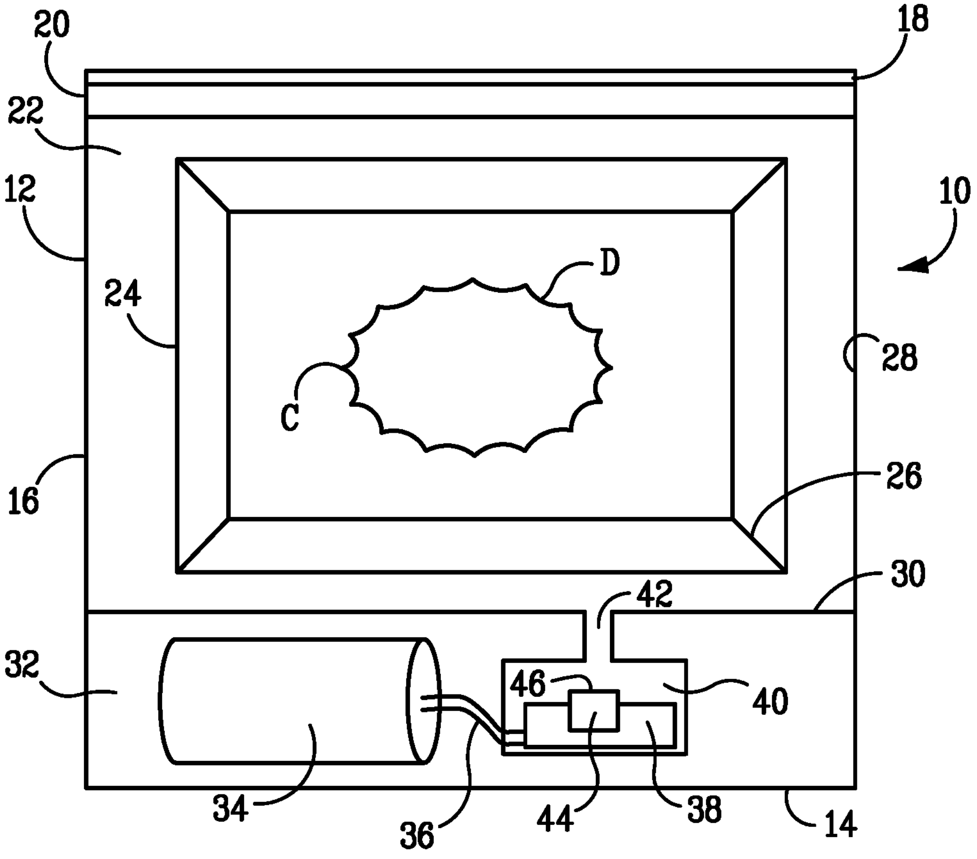
FIG. 1 presents a schematic view of one form of a disposable operating room coating applicator container 10, in accordance herewith.

FIGS. 1-11 provide illustrative, non-exclusive examples of operating room coating applicator containers, in the form of bags, and relate to various methods and systems, according to the present disclosure and/or of systems, apparatus, and/or assemblies that may include, be associated with, be operatively attached to, and/or utilize such containers. In FIGS. 1-11, like numerals denote like, or similar, structures and/or features; and each of the illustrated structures and/or features may not be discussed in detail herein with reference to each of FIGS. 1-11. Similarly, each structure and/or feature may not be explicitly labeled in each of FIGS. 1-11; and any structure and/or feature that is discussed herein with reference to any one of FIGS. 1-11 may be utilized with any other of FIGS. 1-11 without departing from the scope of the present disclosure.

In general, structures and/or features that are, or are likely to be, included in a given embodiment are indicated in solid lines in FIGS. 1-11, while optional structures and/or features are indicated in broken lines. However, a given embodiment is not required to include all structures and/or features that are illustrated in solid lines therein, and any suitable number of such structures and/or features may be omitted from a given embodiment without departing from the scope of the present disclosure.

The medical and surgical devices referenced herein may include surgical instruments and implantable medical devices, wherein the latter may include but are not limited to orthopedic implants for trauma or joint reconstruction, breast implants, sternum closure devices, pacemakers, mono and multifilament sutures, surgical meshes such as hernia repair mesh, hernia plugs, brachy seed spacers, suture clips, suture anchors, adhesion prevention meshes and films, and suture knot clips. Implantable medical devices may be made of absorbable or non-absorbable polymers, or from suitable metals such as stainless steel, titanium and the like.

An absorbable polymer, when exposed to physiological conditions, will degrade and be absorbed by the body over a period of time. Absorbable medical devices typically are formed from generally known, conventional absorbable polymers including, but not limited to, glycolide, lactide, co-polymers of glycolide, or mixtures of polymers, such as polydioxanone, polycaprolactone and equivalents thereof. Preferably, the polymers include polymeric materials selected from the group consisting of greater than about 70% polymerized glycolide, greater than about 70% polymerized lactide, polymerized 1,4-dioxan-2-one, greater than about 70% polypeptide, copolymers of glycolide and lactide, greater than about 70% cellulosics and cellulosic derivatives. Examples of absorbable medical devices may also include mono- and multi-filament sutures. The multi-filament suture may include sutures wherein a plurality of filaments may be formed into a braided structure.

Examples of non-absorbable medical devices may include orthopedic implants for trauma or joint reconstruction, breast implants, sternum closure devices, pacemakers, mono and multifilament sutures, surgical meshes such as hernia repair mesh, hernia plugs and brachy seed spacers, which may be polymeric or nonpolymeric. Non-absorbable polymers include polyolefins, polyamides, polyesters, and polycarbonates and the like.

Suitable antimicrobial agents for the present process may be selected from, but are not limited to, halogenated hydroxyl ethers, acyloxydiphenyl ethers, or combinations thereof. In particular, the antimicrobial agent may be a halogenated 2-hydroxy diphenyl ether and/or a halogenated 2-acyloxy diphenyl ether, or any material having antimicrobial activity which is sublimable or vaporizable at temperatures up to about 300° C. without degrading.

One particularly preferred antimicrobial agent may be 2,4,4'-trichloro-2'-hydroxydiphenyl ether, commonly referred to as triclosan (manufactured by Ciba Geigy under the trade name Irgasan DP300 or Irgacare MP). Triclosan is a broad-spectrum antimicrobial agent that has been used in a variety of products, and is effective against several organisms commonly associated with SSIs. Such microorganisms include, but are not limited to, genus *Staphylococcus, Staphylococcus epidermidis, Staphylococcus aureus*, methicillin-resistant *Staphylococcus epidermidis*, methicillin-resistant *Staphylococcus aureus*, and combinations thereof.

Another particularly preferred antimicrobial agent comprises gentamicin. Gentamicin is also a broad-spectrum antimicrobial agent that has been used in a variety of products, and is also effective against several organisms commonly associated with SSIs, including those listed above.

During the manufacturing process, medical devices may be coated with a composition comprising an antimicrobial agent. The coating may be applied to the device by, for example, dip coating, spray coating, suspended drop coating, or any other coating means. However, such techniques for establishing coatings on packaged surgical devices (implants and/or instruments) during or after their manufacture may present problems. For example, depending on the chemistry and other factors, some coatings may tend to migrate over time from the coated device to its packaging, thereby reducing the amount of coating on the device itself. Again, depending on its chemistry and other factors, some coatings may degrade over time and therefore have a limited shelf-life. Robust sterilization processes that can compromise the integrity of the antimicrobial agent, such as gamma irradiation, e-beam irradiation, heat or steam, are often used in primary sterilization processes. Lastly, a coated, packaged device is subject to handling, which may inadvertently mechanically degrade some coatings. Furthermore, these techniques may have rather extended cycle times and may often require rather large machines to apply the coating, which are not conducive for operation in the limited space of an operating room, where time and space are limited.

Microorganisms of the genus *Staphylococcus* are the most prevalent of all the organisms associated with device-related surgical site infection. *S. aureus* and *S. epidermidis* are commonly present on patients' skin and as such are introduced easily into wounds. One of the most efficacious antimicrobial agents against *Staphylococcus* is 2,4,4'-trichloro-2'-hydroxydiphenyl ether (triclosan). This compound has a minimum inhibitory concentration (MIC) against *S. aureus* of 0.01 ppm, as measured in a suitable growth medium and as described by Bhargava, H. et al in the American Journal of Infection Control, June 1996, pages 209-218. The MIC for a particular antimicrobial agent and a particular microorganism is defined as the minimum concentration of that antimicrobial agent that must be present in an otherwise suitable growth medium for that microorganism, in order to render the growth medium unsuitable for that microorganism, i.e., the minimum concentration to inhibit growth of that microorganism. The phrase "an amount sufficient to substantially inhibit bacterial colonization" as used herein is defined as the minimum inhibitory concentration for *S. aureus* or greater.

A demonstration of this MIC is seen in the disk diffusion method of susceptibility. A filter paper disk, or other object, impregnated with a particular antimicrobial agent is applied to an agar medium that is inoculated with the test organism. Where the anti-microbial agent diffuses through the medium, and as long as the concentration of the antimicrobial agent is above the MIC, none of the susceptible organism will grow on or around the disk for some distance. This distance is called a zone of inhibition. Assuming the antimicrobial agent has a diffusion rate in the medium, the presence of a zone of inhibition around a disk impregnated with an antimicrobial agent indicates that the organism is inhibited by the presence of the antimicrobial agent in the otherwise satisfactory growth medium. The diameter of the zone of inhibition is inversely proportional to the MIC.

Advantageously, the effective concentration of triclosan on the surface of a medical device such as a coated suture may be greater than about 0.01 ppm (wt./wt. coating) or between about 30 ppm to 5,000 ppm (wt./wt. suture). The concentration of triclosan on the surface of package or containment compartment may be between about 5 ppm to 5,000 ppm (wt./wt. package or compartment). For other particular applications, however, higher amounts of antimicrobial agent may be useful and should be considered well within the scope of the present disclosure.

Likewise, the concentration of gentamicin on the surface of a medical device such as a coated suture may be greater than about 0.01 ppm (wt./wt. coating) or between about 30 ppm to 5,000 ppm (wt./wt. suture). The concentration of gentamicin on the surface of package or containment compartment may be between about 5 ppm to 5,000 ppm (wt./wt. package or compartment). Once again, for other particular applications, however, higher amounts of antimicrobial agent may be useful and should be considered well within the scope of the present disclosure.

Referring now to FIG. 1, a schematic view of one form of a disposable operating room coating applicator container 10, in accordance herewith, is presented. As presently conceived and intended to be practiced, disposable coating applicator container 10 of FIG. 1 is structured and arranged to apply a coating of a therapeutic agent C upon an object D to be coated. The disposable coating applicator container 10 includes a sealable container 12, the sealable container 12 having a container bottom 14, the container bottom 14 having upwardly extending walls 16, each upwardly extending wall 16 terminating in an upper edge 18.

Sealable container 12 also includes a closure 20 for sealing a device compartment 22. The device compartment 22 is formed by the upwardly extending walls 16, the closure 20, located adjacent to the upper edges 18 of the upwardly extending walls 16, and a device compartment floor 30. The closure 20 may be in the form of a zip-lock closure, a rib and groove-type closure, or the like, providing a reliable and full closure of the sealable container 12. The disposable coating applicator container 10 comprises a flexible material, such as a polymeric material, or multilayer polymeric composite, and may be in the form of a bag-like structure, as shown.

The device compartment 22 is sized to allow the positioning of object D, which may be an implant or the like, inside the device compartment 22 of sealable container 12. An optional spacer 24, which can be in the form of a wire frame 26, may be positioned in device compartment 22 to ensure adequate gas space around object D. As may be appreciated by those skilled in the art, spacer 24 serves to enable gas or vapor flow inside device compartment 22, making the surfaces or at least a majority of the surfaces of object D accessible to gas or vapor flowing inside device compartment 22 and preventing at least some or most of the surfaces of object D, from touching the inner walls 28 of device compartment 22 and/or from being occluded by the inner walls 28 of device compartment 22.

Disposable operating room coating applicator container 10 also includes a bottom section 32, which may be positioned opposite closure 20. As will be appreciated by those skilled in the art, in other forms, section 20 can be positioned on any side of disposable operating room coating applicator container 10. Bottom section 32 may be configured to be generally separated from device compartment 22.

As shown in FIG. 1, bottom section 32 contains a power supply or battery 34 that is connected by electric leads or traces 36 to a heat source 38. In some forms, the heat source 38 is a resistance heating element 38. An electric switch may be provided (not shown), so that by activating the switch, electric power from battery 34 is supplied to heating element 38 to initiate heating. Within bottom section 32 there is a subcompartment 40 that is connected by a passage or channel 42 that is in fluid communication with device compartment 22, so that gas or vapor can move from subcompartment 40 to device compartment 22 via channel 42.

Still referring to FIG. 1, positioned within subcompartment 40 is a source of evaporable or sublimable medicant or therapeutic agent 44, useful for applying a coating C on object D. Therapeutic agent 44 may be selected from anti-microbial agents, anti-bacterial agents, anti-viral agents, antibiotics, sanitizing agents, or combinations thereof.

In some forms, the therapeutic agent 44 is entrained in a carrier 46. In one form, the therapeutic agent 44 comprises triclosan and is supported on a carrier 46 in the form of an inert patch, such as a porous or absorbent patch, which can be made of any suitable polymer, or natural material, such as non-porous or porous paper, polyethylene, polypropylene, or the like. In some forms, the carrier 46 is positioned adjacent the resistance heating element 38.

Alternatively, the therapeutic agent 44 can be deposited directly into subcompartment 40 or onto the heating element 38. As mentioned, heating element 38 may be positioned within subcompartment 40, or in immediate proximity to subcompartment 40.

In one form, heating element 38 is positioned so as to be in direct contact with therapeutic agent 44. In some forms, the therapeutic agent 44 comprises triclosan and the carrier 46 comprises a sheet, pad or film comprising an absorbable polymer or silicone. In some forms, the absorbable polymer is lactide glycolide copolymer In some forms, a micro-light bulb, such as an LED bulb (not shown), can be installed in the electric circuit and configured to light up when electric power from battery 34 is supplied to heating element 38, providing indication to a user that disposable operating room coating applicator container 10 is operating normally. In some forms, a temperature indicating strip, such as a color-changing temperature indicator (not shown), can also be installed proximal to heating element 38, providing indication to a user that the heating element 38 is hot and that the system is operating normally.

In operation of disposable operating room coating applicator container 10, an object D is positioned inside device compartment 22, and closure 20 is closed. Power supply 34 is then switched on to supply power to heating element 38, which then heats up and increases the temperature of therapeutic agent 44 inside subcompartment 40. Therapeutic agent 44 then evaporates or sublimates and is supplied via channel 42 into device compartment 22, where therapeutic agent 44 redeposits or forms a coating C on the surface of object D.

After sufficient time, such as 1, 3, 5, 10, 20, 60, 120, or 240 min, the power supply 34 is switched off or runs out of power. Closure 20 can be opened (or alternatively sealable container 12 cut open) and the coated object D then removed and used in a surgical procedure.

Advantageously, evaporating or sublimating therapeutic agent 44 is fully contained within disposable operating room coating applicator container 10. Advantageously, only a small portion of disposable operating room coating applicator container 10 is heated, namely subcompartment 40.

Figure 2:
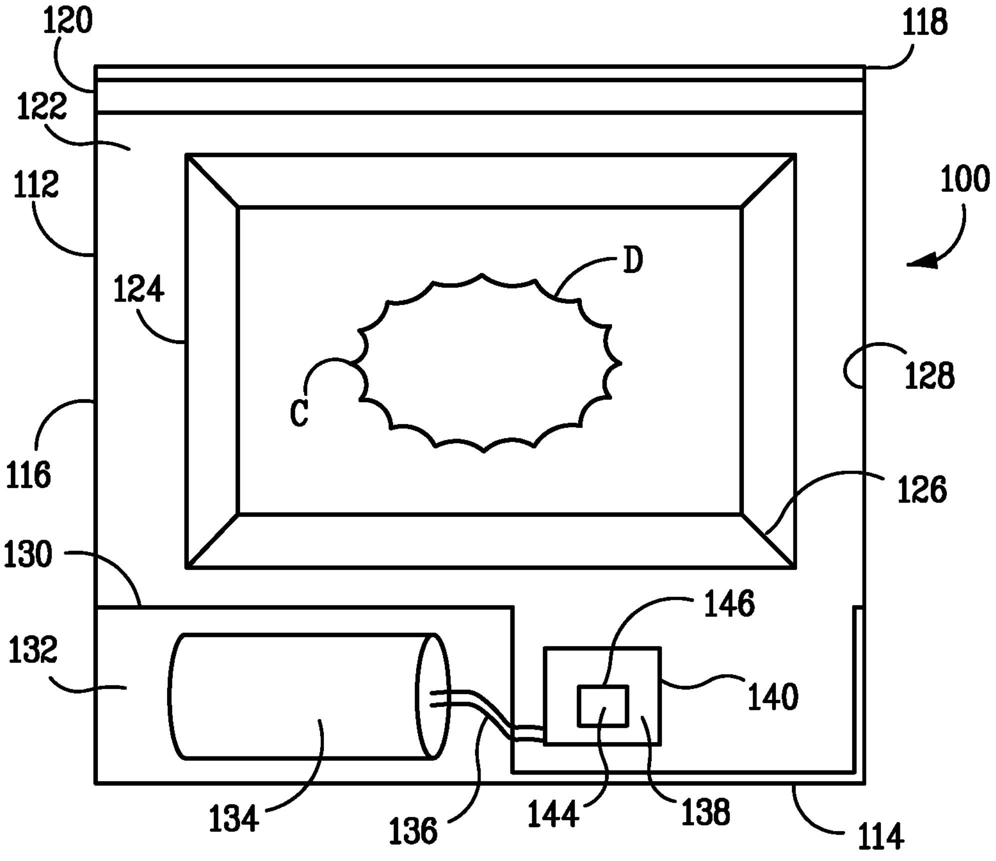
FIG. 2 presents a schematic view of another form of a disposable operating room coating applicator container 100, in accordance herewith.

Referring now to FIG. 2 a schematic view of another form of a disposable operating room coating applicator container 100, in accordance herewith, is presented. Disposable coating applicator container 100 of FIG. 2 is designed to apply a coating of a therapeutic agent C upon an object D to be coated. The disposable coating applicator container 100 includes a sealable container 112, the sealable container 112 having a container bottom 114, the container bottom 114 having upwardly extending walls 116, each upwardly extending wall 116 terminating in an upper edge 118.

Sealable container 112 also includes a closure 120 for sealing a device compartment 122. The device compartment 122 is formed by the upwardly extending walls 116, the closure 120, located adjacent to the upper edges 118 of the upwardly extending walls 116, and a device compartment floor 130. The closure 120 may be in the form of a zip-lock closure, a rib and groove-type closure, or the like, providing a reliable and full closure of the sealable container 112. The disposable coating applicator container 100 comprises a flexible material, such as a polymeric material, or multilayer polymeric composite, and may be in the form of a bag-like structure, as shown.

As with the form of FIG. 1, device compartment 122 is sized to allow the positioning of object D, which again may be an implant or the like, inside the device compartment 122 of sealable container 112. An optional spacer 124, which can be in the form of a wire frame 126, may be positioned in device compartment 122 to ensure adequate gas space around object D. Spacer 124 serves to enable gas or vapor flow inside device compartment 122, making the surfaces or at least a majority of the surfaces of object D accessible to gas or vapor flowing inside device compartment 122 and preventing at least some or most of the surfaces of object D, from touching the inner walls 128 of device compartment 122 and/or from being occluded by the inner walls 128 of device compartment 122.

Disposable operating room coating applicator container 100 also includes a bottom section 132, which may be positioned opposite closure 120. In other forms, bottom section 120 can be positioned on any side of disposable operating room coating applicator container 100. Bottom section 132 may be configured to be generally separated from device compartment 122.

As shown, bottom section 132 contains a power supply or battery 134 that is connected by electric leads or traces 136 to a heat source 138, the heat source 138 positioned within the device compartment 122. In some forms, the heat source 138 is a resistance heating element 138. An electric switch may be provided (not shown), so that by activating the switch, electric power from battery 134 is supplied to heating element 138 to initiate heating.

Still referring to FIG. 2, a subcompartment 140 is provided that is open directly into device compartment 122, with the source of therapeutic agent 144 positioned therein. In one form, heating element 134 is positioned in direct contact with therapeutic agent 144. As may be appreciated, gas or vapor can move from subcompartment 140 to apply a coating C to object D. Therapeutic agent 144 may be selected from anti-microbial agents, anti-bacterial agents, anti-viral agents, antibiotics, sanitizing agents, or combinations thereof.

In some forms, the therapeutic agent 144 is entrained in a carrier 146. In one form, the therapeutic agent 144 comprises triclosan and is supported on a carrier 146 in the form of an inert patch, such as a porous or absorbent patch, which can be made of any suitable polymer, or natural material, such as non-porous or porous paper, polyethylene, polypropylene, or the like. In some forms, the carrier 146 is positioned adjacent the resistance heating element 138. Alternatively, the therapeutic agent 144 can be deposited directly onto the heating element 138.

In one form, heating element 138 is positioned so as to be in direct contact with therapeutic agent 144. In some forms, the therapeutic agent 144 comprises triclosan and the carrier 146 comprises a sheet, pad or film comprising an absorbable polymer or silicone. In some forms, the absorbable polymer is lactide glycolide copolymer In some forms, a micro-light bulb, such as an LED bulb (not shown), can be installed in the electric circuit and configured to light up when electric power from battery 134 is supplied to heating element 138, providing indication to a user that disposable operating room coating applicator container 100 is operating normally. In some forms, a temperature indicating strip, such as a color-changing temperature indicator (not shown), can also be installed proximal to heating element 138, providing indication to a user that the heating element 138 is hot and that the system is operating normally.

In operation of disposable operating room coating applicator container 100, an object D is positioned inside device compartment 122, and closure 120 is closed. Power supply 134 is then switched on to supply power to heating element 138, which then heats up and increases the temperature of therapeutic agent 144. Therapeutic agent 144 then evaporates or sublimates and is supplied into device compartment 122, where therapeutic agent 144 redeposits or forms a coating C on the surface of object D.

After sufficient time, such as 1, 3, 5, 10, 20, 60, 120, or 240 min, the power supply 134 is switched off or runs out of power. Closure 120 can be opened (or alternatively sealable container 112 cut open) and the coated object D then removed and used in a surgical procedure.

Advantageously, evaporating or sublimating therapeutic agent 144 is fully contained within disposable operating room coating applicator container 100.

Figure 3:
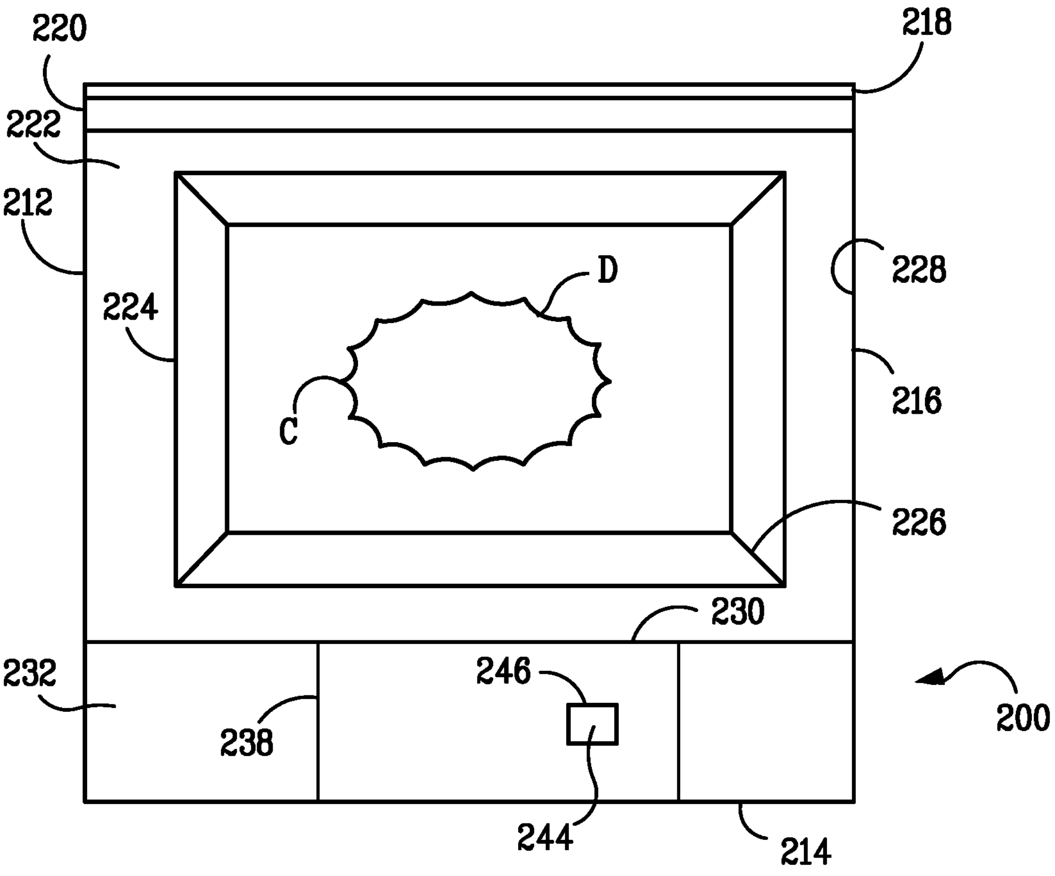
FIG. 3 presents a schematic view of yet another form of a disposable operating room coating applicator container 200, in accordance herewith.

Referring now to FIG. 3, a schematic view of yet another form of a disposable operating room coating applicator container 200, in accordance herewith, is presented. As presently conceived and intended to be practiced, disposable coating applicator container 200 of FIG. 3 is designed and configured to apply a coating of a therapeutic agent C upon an object D to be coated. The disposable coating applicator container 200 includes a sealable container 212, the sealable container 212 having a container bottom 214, the container bottom 214 having upwardly extending walls 216, each upwardly extending wall 216 terminating in an upper edge 218.

Sealable container 212 also includes a closure 220 for sealing a device compartment 222. The device compartment 222 is formed by the upwardly extending walls 216, the closure 220, located adjacent to the upper edges 218 of the upwardly extending walls 216, and a device compartment floor 230. The closure 220 may be, as with the other embodiments described herein, in the form of a zip-lock closure, a rib and groove-type closure, or the like, providing a reliable and full closure of the sealable container 212. The disposable coating applicator container 200 comprises a flexible material, such as a polymeric material, or multilayer polymeric composite, and may be in the form of a bag-like structure, as shown.

The device compartment 222 is sized to allow the positioning of object D, which may be an implant or the like, inside the device compartment 222 of sealable container 212. An optional spacer 224, which can be in the form of a wire frame 226, may be positioned in device compartment 222 to ensure adequate gas space around object D. As may be appreciated by those skilled in the art, spacer 224 serves to enable gas or vapor flow inside device compartment 222, making the surfaces or at least a majority of the surfaces of object D accessible to gas or vapor flowing inside device compartment 222 and preventing at least some or most of the surfaces of object D, from touching the inner walls 228 of device compartment 222 and/or from being occluded by the inner walls 228 of device compartment 222.

Disposable operating room coating applicator container 200 also includes a bottom section 232, which may be positioned opposite closure 220. As will be appreciated by those skilled in the art, in other forms, bottom section 220 can be positioned on any side of disposable operating room coating applicator container 200. Bottom section 232 may be configured to be generally separated from device compartment 222.

Positioned within bottom section 232 is a source of evaporable or sublimable medicant or therapeutic agent 244, useful for applying a coating C on object D. Therapeutic agent 244 may be selected from anti-microbial agents, anti-bacterial agents, anti-viral agents, antibiotics, sanitizing agents, or combinations thereof.

In some forms, the therapeutic agent 244 is entrained in a carrier 246. In one form, the therapeutic agent 244 comprises triclosan and is supported on a carrier 246 in the form of an inert patch, such as a porous or absorbent patch, which can be made of any suitable polymer, or natural material, such as non-porous or porous paper, polyethylene, polypropylene, or the like.

In the form depicted in FIG. 3, bottom section 232 may contain a heat source 238 that provides an exothermic source of heat, such as a heating pack 238, of the type used as a hand-warmer, or the type used for heating ready-to-eat meal kits. Heating pack 238 may be positioned inside the bottom section 232, or outside the bag proximal to therapeutic agent 244. Upon activating the heating pack 238, it rapidly heats thus increasing temperature of therapeutic agent 244.

As may be appreciated, in this form, the source of heat is the chemical reaction or enthalpy of dissolution or crystallization. The heating pack 238 may be activated by unwrapping a semi-permeable pouch (oxygen activated) or snap activated to cause crystallization, or activated by rupturing a water pouch, producing heat due to enthalpy of dissolution. Certain heating packs 238 can heat up very quickly. This is achieved by using an appropriate heating mixture composition (e.g., iron powder, salts, water, active carbon and filler), particle size (e.g., finer particles have higher surface area and accelerate the reaction), and air permeability of the pouch (e.g., high air permeability results in faster heating).

Some fast-acting heat packs are used to heat a food ration for soldiers in the field. For example, U.S. Pat. No. 5,205,277, the contents of which are hereby incorporated by references for these details, discloses a self-heating container which employs calcium oxide that is mixed with a liquid comprised of NaCl, acetic acid, and water. Another example is provided by U.S. Pat. No. 3,976,049, which discloses exothermic compositions consisting of iron powder, a chloride or sulfate, active carbon and water, the contents of which are hereby incorporated by references for these details. Yet another example is provided by U.S. Pat. No. 5,046,479, which discloses similar exothermic compositions based on iron powder, the contents of which are hereby incorporated by references for these details.

Typically, the heat generating composition comprises from about 30% to about 80% iron powder; from about 3% to about 25% activated carbon, non-activated carbon, and mixtures thereof; from about 0.5% to about 10% metal salt; and from about 1% to about 40% water. For faster action, the composition may further include from about 1% to about 20% reactive metal powder such as aluminum or magnesium, or may further include finer iron powder.

Other chemical systems for producing rapid and safe heating action include: calcium chloride, producing heat upon mixing with water that is stored in a frangible pouch; magnesium sulfate (see for example U.S. Pat. No. 4,057,047), also producing heat upon mixing with water; sodium acetate solutions, and the like.

In one form, heating pack 238 is positioned so as to be in direct contact with therapeutic agent 244. In some forms, the therapeutic agent 244 comprises triclosan and the carrier 246 comprises a sheet, pad or film comprising an absorbable polymer or silicone. In some forms, the absorbable polymer is lactide glycolide copolymer.

In some forms, a temperature indicating strip, such as a color-changing temperature indicator (not shown), can also be installed proximal to heating pack 238, providing indication to a user that the heating pack 238 is hot and that the system is operating normally.

In operation of disposable operating room coating applicator container 200, an object D is positioned inside device compartment 222, and closure 220 is closed. Heating pack 238 is activated and increases the temperature of therapeutic agent 244. Therapeutic agent 244 then evaporates or sublimates and is supplied into device compartment 222, where therapeutic agent 244 redeposits or forms a coating C on the surface of object D.

After sufficient time, such as 1, 3, 5, 10, 20, 60, 120, or 240 min, closure 20 can be opened (or alternatively sealable container 212 cut open) and the coated object D then removed and used in a surgical procedure.

Advantageously, evaporating or sublimating therapeutic agent 244 is fully contained within disposable operating room coating applicator container 200.

Figure 4:
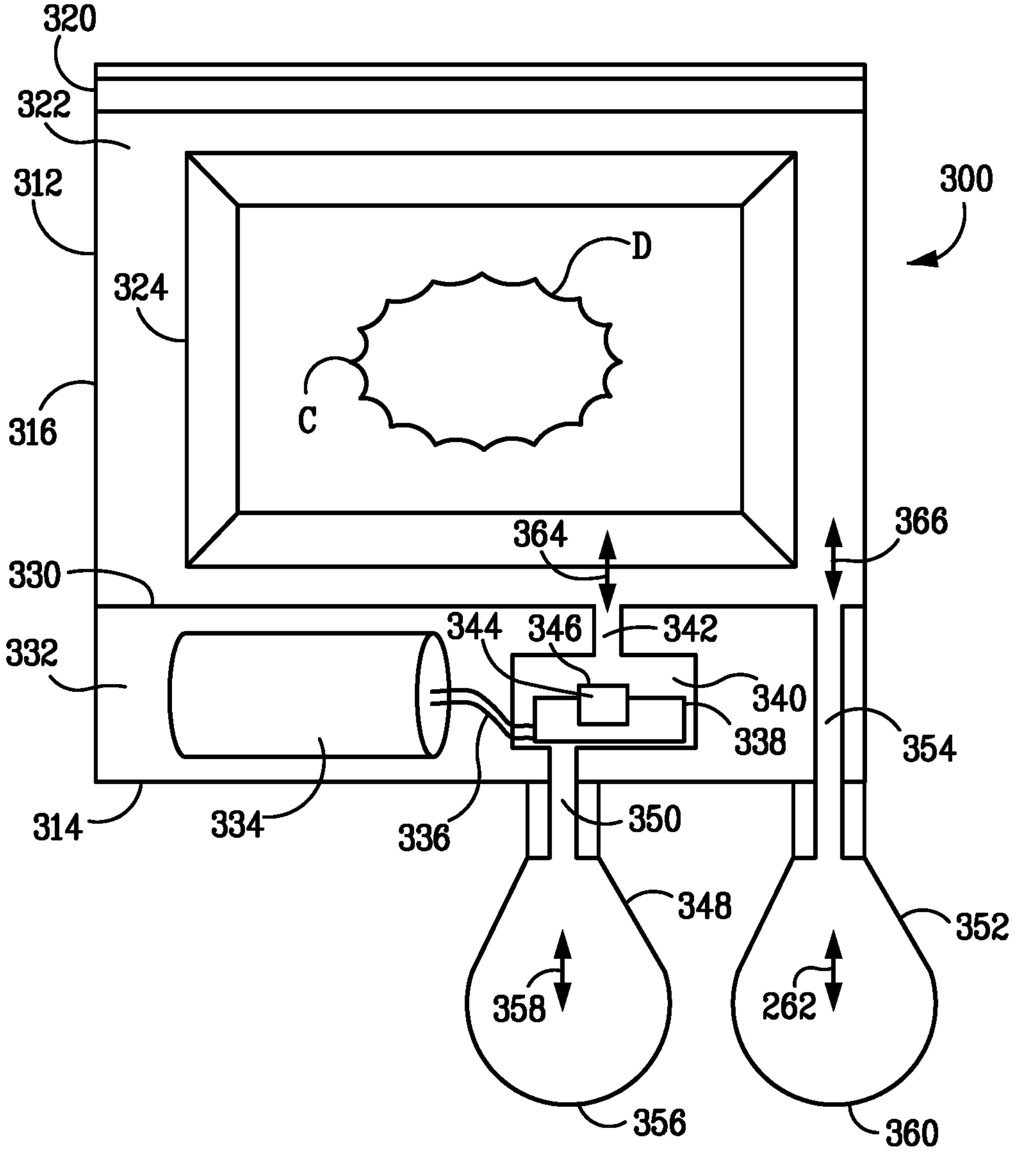
FIG. 4 presents a schematic view of still yet another form of a disposable operating room coating applicator container 300, in accordance herewith.

Referring now to FIG. 4, a schematic view of one form of a disposable operating room coating applicator container 300, in accordance herewith, is presented. As presently conceived and intended to be practiced, disposable coating applicator container 300 of FIG. 4 is structured and arranged to apply a coating of a therapeutic agent C upon an object D to be coated. The disposable coating applicator container 300 includes a sealable container 312, the sealable container 312 having a container bottom 314, the container bottom 314 having upwardly extending walls 316, each upwardly extending wall 316 terminating in an upper edge 318.

Sealable container 312 also includes a closure 320 for sealing a device compartment 322. The device compartment 322 is formed by the upwardly extending walls 316, the closure 320, located adjacent to the upper edges 318 of the upwardly extending walls 316, and a device compartment floor 330. The closure 320 may be in the form of a zip-lock closure, a rib and groove-type closure, or the like, providing a reliable and full closure of the sealable container 312. The disposable coating applicator container 300 comprises a flexible material, such as a polymeric material, or multilayer polymeric composite, and may be in the form of a bag-like structure, as shown.

The device compartment 322 is sized to allow the positioning of object D, which may be an implant or the like, inside the device compartment 322 of sealable container 312. An optional spacer 324, which can be in the form of a wire frame 326, may be positioned in device compartment 322 to ensure adequate gas space around object D. As may be appreciated by those skilled in the art, spacer 324 serves to enable gas or vapor flow inside device compartment 322, making the surfaces or at least a majority of the surfaces of object D accessible to gas or vapor flowing inside device compartment 322 and preventing at least some or most of the surfaces of object D, from touching the inner walls 328 of device compartment 322 and/or from being occluded by the inner walls 328 of device compartment 322.

Disposable operating room coating applicator container 300 also includes a bottom section 332, which may be positioned opposite closure 320. As will be appreciated by those skilled in the art, in other forms, bottom section 332 can be positioned on any side of disposable operating room coating applicator container 300. Bottom section 332 may be configured to be generally separated from device compartment 322.

As shown in FIG. 4, bottom section 332 contains a power supply or battery 334 that is connected by electric leads or traces 336 to a heat source 338. In some forms, the heat source 338 is a resistance heating element 338. An electric switch may be provided (not shown), so that by activating the switch, electric power from battery 334 is supplied to heating element 338 to initiate heating. Within bottom section 332 there is a subcompartment 340 that is connected by a passage or channel 342 that is in fluid communication with device compartment 322, so that gas or vapor can move from subcompartment 340 to device compartment 322 via channel 342.

Still referring to FIG. 4, positioned within subcompartment 340 is a source of evaporable or sublimable medicant or therapeutic agent 344, useful for applying a coating C on object D. Therapeutic agent 344 may be selected from anti-microbial agents, anti-bacterial agents, anti-viral agents, antibiotics, sanitizing agents, or combinations thereof.

In some forms, the therapeutic agent 344 is entrained in a carrier 346. In one form, the therapeutic agent 344 comprises triclosan and is supported on a carrier 346 in the form of an inert patch, such as a porous or absorbent patch, which can be made of any suitable polymer, or natural material, such as non-porous or porous paper, polyethylene, polypropylene, or the like. In some forms, the carrier 346 is positioned adjacent the resistance heating element 338.

Alternatively, the therapeutic agent 344 can be deposited directly into subcompartment 340 or onto the heating element 338. As mentioned, heating element 338 may be positioned within subcompartment 340, or in immediate proximity to subcompartment 340.

In one form, heating element 338 is positioned so as to be in direct contact with therapeutic agent 344. In some forms, the therapeutic agent 344 comprises triclosan and the carrier 346 comprises a sheet, pad or film comprising an absorbable polymer or silicone. In some forms, the absorbable polymer is lactide glycolide copolymer.

As shown in FIG. 4, disposable operating room coating applicator container 300 also includes a manual vapor circulating pump 348, such as a compressible elastic bulb or bellows, connected to disposable operating room coating applicator container 300. Vapor circulating pump 348 is in fluid communication with subcompartment 340 via channel 350 and is further also in fluid communication with device compartment 322 via channel 342.

In one form, disposable operating room coating applicator container 300 includes a manual gas circulating pump 352, such as compressible elastic bulb or bellows, connected to disposable operating room coating applicator container 300. Gas circulating pump 352 is in fluid communication with device compartment 322 via channel 354.

In some forms, a micro-light bulb, such as an LED bulb (not shown), can be installed in the electric circuit and configured to light up when electric power from battery 334 is supplied to heating element 338, providing indication to a user that disposable operating room coating applicator container 300 is operating normally. In some forms, a temperature indicating strip, such as a color-changing temperature indicator (not shown), can also be installed proximal to heating element 338, providing indication to a user that the heating element 338 is hot and that the system is operating normally.

In some forms only vapor circulating pump 348 is present. In some forms, only gas circulating pump 352 is present. In some forms, both vapor circulating pump 348 and gas circulating pump 352 are present.

In operation of disposable operating room coating applicator container 300, an object D is positioned inside device compartment 322, and closure 320 is closed. Power supply 334 is then switched on to supply power to heating element 338, which then heats up and increases the temperature of therapeutic agent 344 inside subcompartment 340.

Concurrent with the heating of heating element 338, vapor circulating pump 348 and/or gas circulating pump 352 can be actuated as follows. Vapor circulating pump 352 is actuated by compressing and releasing bulb 356 and thus moving gas (such as air) via channel 350 into device compartment 322 via channel 342 and out of device compartment 322 via channel 342, as shown by arrows 358, thus facilitating exchange and uniform deposition of therapeutic agent 344 on the surface of object D.

Gas circulating pump 352 is actuated by compressing and releasing bulb 360 and thus moving gas via channel 354 into device compartment 322, and then back, as shown by arrows 362, thus facilitating exchange and uniform deposition of therapeutic agent 344 on the surface of object D.

In some embodiments, vapor circulating pump 348 can be operated on its own or gas circulating pump 352 can be operated on its own, or alternatively both vapor circulating pump 348 and gas circulating pump 352 can be operated simultaneously.

In one form, when vapor circulating pump 348 is compressed, moving gas via channel 350 into subcompartment 340, then into device compartment 322 via channel 342, gas circulating pump 352 is simultaneously released, facilitating intake of gas via channel 354 from device compartment 322 into gas circulating pump 352.

Once the necessary changes have been made when vapor circulating pump 60 is released, moving gas from device compartment 322 and into subcompartment 340 via channel 342 and then via channel 350 into vapor circulating pump 348, gas circulating pump 352 is simultaneously compressed, moving gas from gas circulating pump 352 via channel 354 into device compartment 322.

Therapeutic agent 344 evaporates or sublimates and redeposits on surface of object C. After sufficient time, such as 1, 3, 5, 10, 20, 60, 120, or 240 min, the power supply 34 is switched off or runs out of power. Closure 320 can be opened (or alternatively sealable container 312 cut open) and the coated object D then removed and used in a surgical procedure.

Advantageously, evaporating or sublimating therapeutic agent 344 is fully contained within disposable operating room coating applicator container 300. Advantageously, only a small portion of disposable operating room coating applicator container 300 is heated, namely subcompartment 340.

Figure 5:
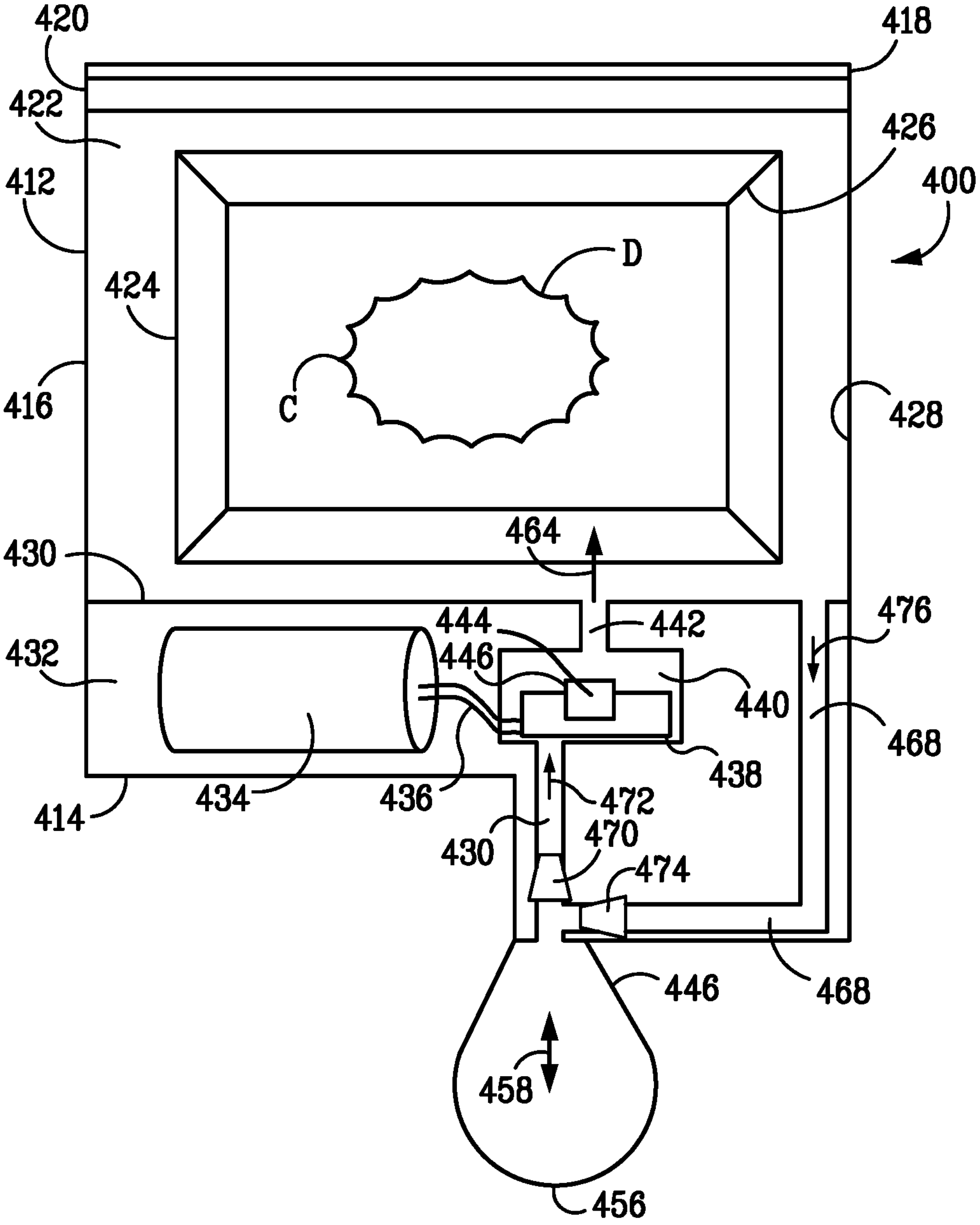
FIG. 5 presents a schematic view of another form of a disposable operating room coating applicator container 400, in accordance herewith.

Referring now to FIG. 5, a schematic view of one form of a disposable operating room coating applicator container 400, in accordance herewith, is presented. As presently conceived and intended to be practiced, disposable coating applicator container 400 of FIG. 5 is designed to apply a coating of a therapeutic agent C upon an object D to be coated. The disposable coating applicator container 400 includes a sealable container 412, the sealable container 412 having a container bottom 414, the container bottom 414 having upwardly extending walls 416, each upwardly extending wall 416 terminating in an upper edge 418.

Sealable container 412 also includes a closure 420 for sealing a device compartment 422. The device compartment 422 is formed by the upwardly extending walls 416, the closure 420, located adjacent to the upper edges 418 of the upwardly extending walls 416, and a device compartment floor 430. The closure 420 may be in the form of a zip-lock closure, a rib and groove-type closure, or the like, providing a reliable and full closure of the sealable container 412. The disposable coating applicator container 400 comprises a flexible material, such as a polymeric material, or multilayer polymeric composite, and may be in the form of a bag-like structure, as shown.

The device compartment 422 is sized to allow the positioning of object D, which may be an implant or the like, inside the device compartment 422 of sealable container 412. An optional spacer 424, which can be in the form of a wire frame 426, may be positioned in device compartment 422 to ensure adequate gas space around object D. As may be appreciated by those skilled in the art, spacer 424 serves to enable gas or vapor flow inside device compartment 422, making the surfaces or at least a majority of the surfaces of object D accessible to gas or vapor flowing inside device compartment 422 and preventing at least some or most of the surfaces of object D, from touching the inner walls 428 of device compartment 422 and/or from being occluded by the inner walls 428 of device compartment 422.

Disposable operating room coating applicator container 400 also includes a bottom section 432, which may be positioned opposite closure 420. As will be appreciated by those skilled in the art, in other forms, bottom section 432 can be positioned on any side of disposable operating room coating applicator container 400. Bottom section 432 may be configured to be generally separated from device compartment 422.

As shown in FIG. 5, bottom section 432 contains a power supply or battery 434 that is connected by electric leads or traces 436 to a heat source 438. In some forms, the heat source 438 is a resistance heating element 438. An electric switch may be provided (not shown), so that by activating the switch, electric power from battery 434 is supplied to heating element 438 to initiate heating. Within bottom section 432, there is a subcompartment 440 that is connected by a passage or channel 442 that is in fluid communication with device compartment 422, so that gas or vapor can move from subcompartment 440 to device compartment 422 via channel 442.

Positioned within subcompartment 440 is a source of evaporable or sublimable medicant or therapeutic agent 444, useful for applying a coating C on object D. Therapeutic agent 444 may be selected from anti-microbial agents, anti-bacterial agents, anti-viral agents, antibiotics, sanitizing agents, or combinations thereof.

In some forms, the therapeutic agent 444 is entrained in a carrier 446. In one form, the therapeutic agent 444 comprises triclosan and is supported on a carrier 446 in the form of an inert patch, such as a porous or absorbent patch, which can be made of any suitable polymer, or natural material, such as non-porous or porous paper, polyethylene, polypropylene, or the like. In some forms, the carrier 446 is positioned adjacent the resistance heating element 438.

Alternatively, the therapeutic agent 444 can be deposited directly into subcompartment 440 or onto the heating element 438. As mentioned, heating element 438 may be positioned within subcompartment 440, or in immediate proximity to subcompartment 440.

In one form, heating element 438 is positioned so as to be in direct contact with therapeutic agent 444. In some forms, the therapeutic agent 444 comprises triclosan and the carrier 446 comprises a sheet, pad or film comprising an absorbable polymer or silicone. In some forms, the absorbable polymer is lactide glycolide copolymer.

As shown in FIG. 5, disposable operating room coating applicator container 400 also includes a manual recirculating pump 448, such as a compressible elastic bulb or bellows, connected to disposable operating room coating applicator container 400. Recirculating pump 448 is in fluid communication with subcompartment 440 via channel 450 and is further also in fluid communication with device compartment 422 via channel 442. Recirculating pump 448 is also in fluid communication with device compartment 422 via separate gas intake channel 468.

The bulb 456 of recirculating pump 448 can be compressed and released, resulting in movement of gas out of or into bulb of recirculating pump 448, as shown by arrow 458. A one-way supply valve 470 is installed in vapor supply channel 450 and configured to allow gas to move from recirculating pump 448 into vapor supply channel 450 and further into subcompartment 440 and further into device compartment 422 via channel 468, as shown by arrow 472. One-way supply valve 470 prevents gas from moving directly from subcompartment 440 into vapor supply channel 450 and into recirculating pump 448.

A one-way intake valve 474 is installed in gas intake channel 468 and configured to allow gas to move from device compartment 422 and into recirculating pump 458 as shown by arrows 476. One-way intake valve 474 prevents any gas from moving from recirculating pump 458 directly into gas intake channel 468.

In some forms, a micro-light bulb, such as an LED bulb (not shown), can be installed in the electric circuit and configured to light up when electric power from battery 434 is supplied to heating element 438, providing indication to a user that disposable operating room coating applicator container 400 is operating normally. In some forms, a temperature indicating strip, such as a color-changing temperature indicator (not shown), can also be installed proximal to heating element 438, providing indication to a user that the heating element 438 is hot and that the system is operating normally.

In operation of disposable operating room coating applicator container 400, an object D is positioned inside device compartment 422, and closure 420 is closed. Power supply 434 is then switched on to supply power to heating element 438, which then heats up and increases the temperature of therapeutic agent 444 inside subcompartment 440.

Concurrent with the heating of element 434, recirculating pump 458 is compressing and then releasing bulb 456 and thus moving gas (such as air) via channel 450 through one-way supply valve 470 into subcompartment 440, where gas can pick-up the vapor of therapeutic agent 444, and then transfer that vapor into device compartment 422 via channel 442, as shown by arrow 464. Gas then can flow back, as shown by arrows 476, from device compartment 422 into recirculating pump 458 via gas intake channel 468 and one-way intake valve 474, thus facilitating exchange and uniform deposition of therapeutic agent 444 on the surface of object D.

After sufficient time, such as 1, 3, 5, 10, 20, 60, 120, or 240 min, the power supply 434 is switched off or runs out of power. Closure 420 can be opened (or alternatively sealable container 412 cut open) and the coated object D then removed and used in a surgical procedure.

Advantageously, evaporating or sublimating therapeutic agent 444 is fully contained within disposable operating room coating applicator container 400. Advantageously, only a small portion of disposable operating room coating applicator container 400 is heated, namely subcompartment 440.

Figure 6:
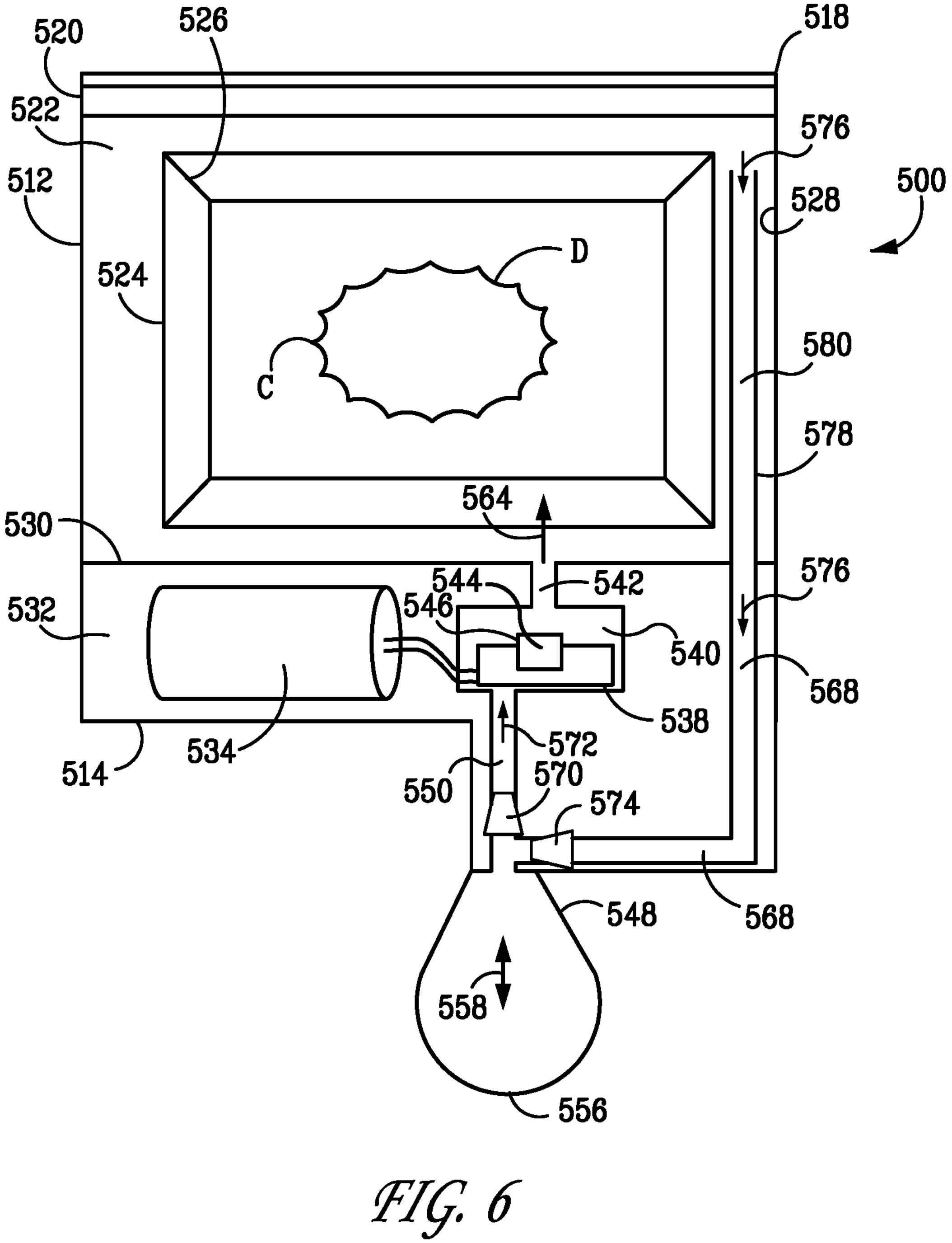
FIG. 6 presents a schematic view of yet another form of a disposable operating room coating applicator container 500, in accordance herewith.

Referring now to FIG. 6, a schematic view of one form of a disposable operating room coating applicator container 500, in accordance herewith, is presented. As presently conceived and intended to be practiced, disposable coating applicator container 500 of FIG. 6 is designed to apply a coating of a therapeutic agent C upon an object D to be coated. The disposable coating applicator container 500 includes a sealable container 512, the sealable container 512 having a container bottom 514, the container bottom 514 having upwardly extending walls 516, each upwardly extending wall 516 terminating in an upper edge 518.

Sealable container 512 also includes a closure 520 for sealing a device compartment 522. The device compartment 522 is formed by the upwardly extending walls 516, the closure 520, located adjacent to the upper edges 518 of the upwardly extending walls 516, and a device compartment floor 530. The closure 520 may be in the form of a zip-lock closure, a rib and groove-type closure, or the like, providing a reliable and full closure of the sealable container 512. The disposable coating applicator container 500 comprises a flexible material, such as a polymeric material, or multilayer polymeric composite, and may be in the form of a bag-like structure, as shown.

The device compartment 522 is sized to allow the positioning of object D, which may be an implant or the like, inside the device compartment 522 of sealable container 512. An optional spacer 524, which can be in the form of a wire frame 526, may be positioned in device compartment 522 to ensure adequate gas space around object D. As may be appreciated by those skilled in the art, spacer 524 serves to enable gas or vapor flow inside device compartment 522, making the surfaces or at least a majority of the surfaces of object D accessible to gas or vapor flowing inside device compartment 522 and preventing at least some or most of the surfaces of object D, from touching the inner walls 528 of device compartment 522 and/or from being occluded by the inner walls 528 of device compartment 522.

Disposable operating room coating applicator container 500 also includes a bottom section 532, which may be positioned opposite closure 520. As will be appreciated by those skilled in the art, in other forms, bottom section 532 can be positioned on any side of disposable operating room coating applicator container 500. Bottom section 532 may be configured to be generally separated from device compartment 522.

As shown in FIG. 6, bottom section 532 contains a power supply or battery 534 that is connected by electric leads or traces 536 to a heat source 538. In some forms, the heat source 538 is a resistance heating element 538. An electric switch may be provided (not shown), so that by activating the switch, electric power from battery 534 is supplied to heating element 538 to initiate heating. Within bottom section 532, there is a subcompartment 540 that is connected by a passage or channel 542 that is in fluid communication with device compartment 522, so that gas or vapor can move from subcompartment 540 to device compartment 522 via channel 542.

Positioned within subcompartment 540 is a source of evaporable or sublimable medicant or therapeutic agent 544, useful for applying a coating C on object D. Therapeutic agent 544 may be selected from anti-microbial agents, anti-bacterial agents, anti-viral agents, antibiotics, sanitizing agents, or combinations thereof.

In some forms, the therapeutic agent 544 is entrained in a carrier 546. In one form, the therapeutic agent 544 comprises triclosan and is supported on a carrier 546 in the form of an inert patch, such as a porous or absorbent patch, which can be made of any suitable polymer, or natural material, such as non-porous or porous paper, polyethylene, polypropylene, or the like. In some forms, the carrier 546 is positioned adjacent the resistance heating element 538.

Alternatively, the therapeutic agent 544 can be deposited directly into subcompartment 540 or onto the heating element 538. As mentioned, heating element 538 may be positioned within subcompartment 540, or in immediate proximity to subcompartment 540.

In one form, heating element 538 is positioned so as to be in direct contact with therapeutic agent 544. In some forms, the therapeutic agent 544 comprises triclosan and the carrier 546 comprises a sheet, pad or film comprising an absorbable polymer or silicone. In some forms, the absorbable polymer is lactide glycolide copolymer.

As shown in FIG. 6, disposable operating room coating applicator container 500 also includes a manual recirculating pump 548, such as a compressible elastic bulb or bellows, connected to disposable operating room coating applicator container 500. Recirculating pump 548 is in fluid communication with subcompartment 540 via channel 550 and is further also in fluid communication with device compartment 522 via channel 542.

Recirculating pump 548 is also in fluid communication with device compartment 522 via separate gas intake channel 568, which is in fluid communication with an intake cannula 578, which may be in the form of a polymeric tube 580, that is connected to gas intake channel 568 and terminates in device compartment 522 distally to channel 542, such as in the middle of device compartment 522 (not shown) or proximal to closure 520 (as shown).

Intake cannula 578 serves for facilitating gas flow back, as shown by arrows 576, from device compartment 522 into recirculating pump 548 via gas intake channel 568 and one-way intake valve 574. This arrangement facilitates good exchange of gas and vapor throughout device compartment 522, with gas containing therapeutic agent 544 vapor entering device compartment 522 on one side of disposable operating room coating applicator container 500, as shown by arrow 572, proximal to bottom section 532, with gas then moving about device compartment 522 prior to exiting via intake cannula 578 remote to bottom section 532.

Advantageously, intake cannula 578 further facilitates good exchange and uniform deposition of therapeutic agent 544 on the surface of object D.

The bulb 556 of recirculating pump 548 can be compressed and released, resulting in movement of gas out of or into bulb of recirculating pump 548, as shown by arrow 558. A one-way supply valve 570 is installed in vapor supply channel 550 and configured to allow gas to move from recirculating pump 548 into vapor supply channel 550 and further into subcompartment 540 and further into device compartment 522 via channel 568, as shown by arrow 572. One-way supply valve 570 prevents gas from moving directly from subcompartment 540 into vapor supply channel 550 and into recirculating pump 548.

A one-way intake valve 574 is installed in gas intake channel 568 and configured to allow gas to move from device compartment 522 and into recirculating pump 558 as shown by arrows 576. One-way intake valve 574 prevents any gas from moving from recirculating pump 558 directly into gas intake channel 568 and intake cannula 578.

In some forms, a micro-light bulb, such as an LED bulb (not shown), can be installed in the electric circuit and configured to light up when electric power from battery 534 is supplied to heating element 538, providing indication to a user that disposable operating room coating applicator container 500 is operating normally. In some forms, a temperature indicating strip, such as a color-changing temperature indicator (not shown), can also be installed proximal to heating element 538, providing indication to a user that the heating element 538 is hot and that the system is operating normally.

In operation of disposable operating room coating applicator container 500, an object D is positioned inside device compartment 522, and closure 520 is closed. Power supply 534 is then switched on to supply power to heating element 538, which then heats up and increases the temperature of therapeutic agent 544 inside subcompartment 540.

Concurrent with the heating of element 534, recirculating pump 558 is compressing and then releasing bulb 556 and thus moving gas (such as air) via channel 550 through one-way supply valve 570 into subcompartment 540, where gas can pick-up the vapor of therapeutic agent 544, and then transfer that vapor into device compartment 522 via channel 542, as shown by arrow 564. Gas then can flow back, as shown by arrows 576, from device compartment 522 into recirculating pump 558 via gas intake channel 568 and intake cannula 578 and one-way intake valve 574, thus facilitating exchange and uniform deposition of therapeutic agent 544

After sufficient time, such as 1, 3, 5, 10, 20, 60, 120, or 240 min, the power supply 534 is switched off or runs out of power. Closure 520 can be opened (or alternatively sealable container 512 cut open) and the coated object D then removed and used in a surgical procedure.

Advantageously, evaporating or sublimating therapeutic agent 544 is fully contained within disposable operating room coating applicator container 500. Advantageously, only a small portion of disposable operating room coating applicator container 500 is heated, namely subcompartment 540.

Figure 7:
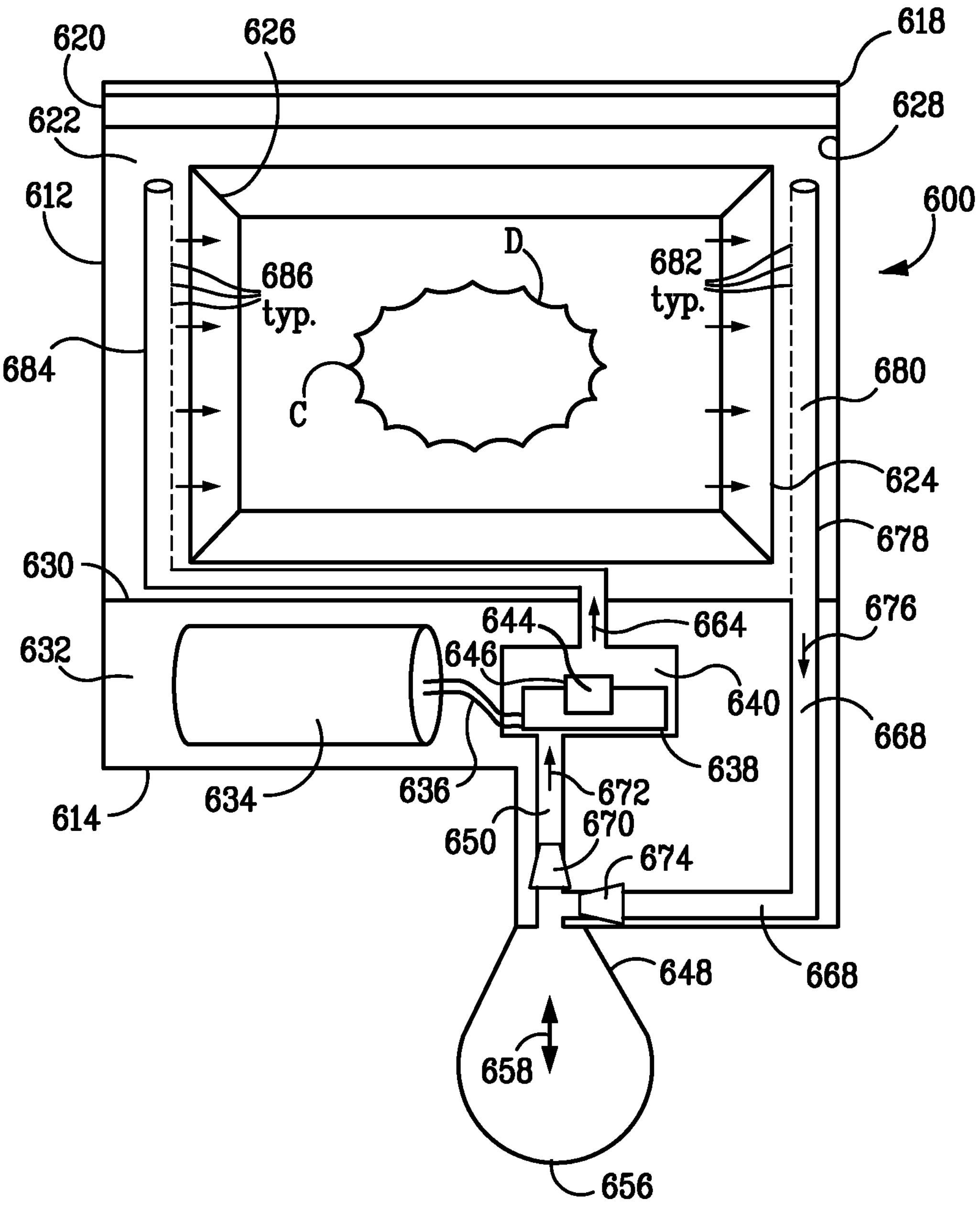
FIG. 7 presents a schematic view of still yet another form of a disposable operating room coating applicator container 600, in accordance herewith.

Referring now to FIG. 7, a schematic view of one form of a disposable operating room coating applicator container 600, in accordance herewith, is presented. As presently conceived and intended to be practiced, disposable coating applicator container 600 of FIG. 7 is designed to apply a coating of a therapeutic agent C upon an object D to be coated. The disposable coating applicator container 600 includes a sealable container 612, the sealable container 612 having a container bottom 614, the container bottom 614 having upwardly extending walls 616, each upwardly extending wall 616 terminating in an upper edge 618.

Sealable container 612 also includes a closure 620 for sealing a device compartment 622. The device compartment 622 is formed by the upwardly extending walls 616, the closure 620, located adjacent to the upper edges 618 of the upwardly extending walls 616, and a device compartment floor 630. The closure 620 may be in the form of a zip-lock closure, a rib and groove-type closure, or the like, providing a reliable and full closure of the sealable container 612. The disposable coating applicator container 600 comprises a flexible material, such as a polymeric material, or multilayer polymeric composite, and may be in the form of a bag-like structure, as shown.

The device compartment 622 is sized to allow the positioning of object D, which may be an implant or the like, inside the device compartment 622 of sealable container 612. An optional spacer 624, which can be in the form of a wire frame 626, may be positioned in device compartment 622 to ensure adequate gas space around object D. As may be appreciated by those skilled in the art, spacer 624 serves to enable gas or vapor flow inside device compartment 622, making the surfaces or at least a majority of the surfaces of object D accessible to gas or vapor flowing inside device compartment 622 and preventing at least some or most of the surfaces of object D, from touching the inner walls 628 of device compartment 622 and/or from being occluded by the inner walls 628 of device compartment 622.

Disposable operating room coating applicator container 600 also includes a bottom section 632, which may be positioned opposite closure 620. As will be appreciated by those skilled in the art, in other forms, bottom section 632 can be positioned on any side of disposable operating room coating applicator container 600. Bottom section 632 may be configured to be generally separated from device compartment 622.

As shown in FIG. 7, bottom section 632 contains a power supply or battery 634 that is connected by electric leads or traces 636 to a heat source 638. In some forms, the heat source 638 is a resistance heating element 638. An electric switch may be provided (not shown), so that by activating the switch, electric power from battery 634 is supplied to heating element 638 to initiate heating. Within bottom section 632, there is a subcompartment 640 that is connected by a passage or channel 642 that is in fluid communication with device compartment 622, so that gas or vapor can move from subcompartment 640 to device compartment 622 via channel 642.

Positioned within subcompartment 640 is a source of evaporable or sublimable medicant or therapeutic agent 644, useful for applying a coating C on object D. Therapeutic agent 644 may be selected from anti-microbial agents, anti-bacterial agents, anti-viral agents, antibiotics, sanitizing agents, or combinations thereof.

In some forms, the therapeutic agent 644 is entrained in a carrier 646. In one form, the therapeutic agent 644 comprises triclosan and is supported on a carrier 646 in the form of an inert patch, such as a porous or absorbent patch, which can be made of any suitable polymer, or natural material, such as non-porous or porous paper, polyethylene, polypropylene, or the like. In some forms, the carrier 646 is positioned adjacent the resistance heating element 638.

Alternatively, the therapeutic agent 644 can be deposited directly into subcompartment 640 or onto the heating element 638. As mentioned, heating element 638 may be positioned within subcompartment 640, or in immediate proximity to subcompartment 640.

In one form, heating element 638 is positioned so as to be in direct contact with therapeutic agent 644. In some forms, the therapeutic agent 644 comprises triclosan and the carrier 646 comprises a sheet, pad or film comprising an absorbable polymer or silicone. In some forms, the absorbable polymer is lactide glycolide copolymer.

As shown in FIG. 7, disposable operating room coating applicator container 600 also includes a manual recirculating pump 648, such as a compressible elastic bulb or bellows, connected to disposable operating room coating applicator container 600. Recirculating pump 648 is in fluid communication with subcompartment 640 via channel 650 and is further also in fluid communication with device compartment 622 via channel 642.

Recirculating pump 648 is also in fluid communication with device compartment 622 via separate gas intake channel 668, which is in fluid communication with an intake cannula 678, which may be in the form of a polymeric tube 680, that is connected to gas intake channel 668 and terminates in device compartment 622 distally to channel 642, such as in the middle of device compartment 622 (not shown) or proximal to closure 620 (as shown).

Intake cannula 678 serves to facilitate gas flow back, as shown by arrows 676, from device compartment 622 into recirculating pump 648 via gas intake channel 668 and one-way intake valve 674. This arrangement facilitates good exchange of gas and vapor throughout device compartment 622, with gas containing therapeutic agent 644 vapor entering device compartment 622 on one side of disposable operating room coating applicator container 600, as shown by arrow 672, proximal to bottom section 632, with gas then moving about device compartment 622 prior to exiting via intake cannula 678 remote to bottom section 632.

In the form depicted in FIG. 7, intake cannula 678, is provided with a plurality of apertures 682 to collect gas over an area of device compartment 622 and return it to the recirculating pump 648 and source of evaporating/sublimating therapeutic agent 644. Advantageously, intake cannula 678 further facilitates good exchange and uniform deposition of therapeutic agent 644 on the surface of object D.

Further, a gas and therapeutic agent supply cannula 684, having apertures 686, as shown, is provided to supply gas and therapeutic agent 644 over an area of device compartment 622. Supply cannula 684 may be positioned opposite intake cannula 678, thus facilitating gas and therapeutic agent 644 movement across device compartment 622.

The bulb 656 of recirculating pump 648 can be compressed and released, resulting in movement of gas out of or into bulb of recirculating pump 648, as shown by arrow 658. A one-way supply valve 670 is installed in vapor supply channel 650 and configured to allow gas to move from recirculating pump 648 into vapor supply channel 650 and further into subcompartment 640 and further into device compartment 622 via channel 668, as shown by arrow 672. One-way supply valve 670 prevents gas from moving directly from subcompartment 640 into vapor supply channel 650 and into recirculating pump 648.

A one-way intake valve 674 is installed in gas intake channel 668 and configured to allow gas to move from device compartment 622 and into recirculating pump 658 as shown by arrows 676. One-way intake valve 674 prevents any gas from moving from recirculating pump 658 directly into gas intake channel 568 and intake cannula 678.

In some forms, a micro-light bulb, such as an LED bulb (not shown), can be installed in the electric circuit and configured to light up when electric power from battery 634 is supplied to heating element 638, providing indication to a user that disposable operating room coating applicator container 600 is operating normally. In some forms, a temperature indicating strip, such as a color-changing temperature indicator (not shown), can also be installed proximal to heating element 638, providing indication to a user that the heating element 638 is hot and that the system is operating normally.

In operation of disposable operating room coating applicator container 600, an object D is positioned inside device compartment 622, and closure 620 is closed. Power supply 634 is then switched on to supply power to heating element 638, which then heats up and increases the temperature of therapeutic agent 644 inside subcompartment 640.

Concurrent with the heating of element 634, recirculating pump 658 is compressing and then releasing bulb 656 and thus moving gas (such as air) via channel 650 through one-way supply valve 670 into subcompartment 640, where gas can pick-up the vapor of therapeutic agent 644, and then transfer that vapor into device compartment 622 via channel 642, as shown by arrow 664. Gas then can flow back, as shown by arrows 676, from device compartment 622 into recirculating pump 658 via gas intake channel 668 and intake cannula 678 and one-way intake valve 674, thus facilitating exchange and uniform deposition of therapeutic agent 644

After sufficient time, such as 1, 3, 5, 10, 20, 60, 120, or 240 min, the power supply 634 is switched off or runs out of power. Closure 620 can be opened (or alternatively sealable container 612 cut open) and the coated object D then removed and used in a surgical procedure.

Advantageously, evaporating or sublimating therapeutic agent 644 is fully contained within disposable operating room coating applicator container 600. Advantageously, only a small portion of disposable operating room coating applicator container 600 is heated, namely subcompartment 640.

Figure 8:
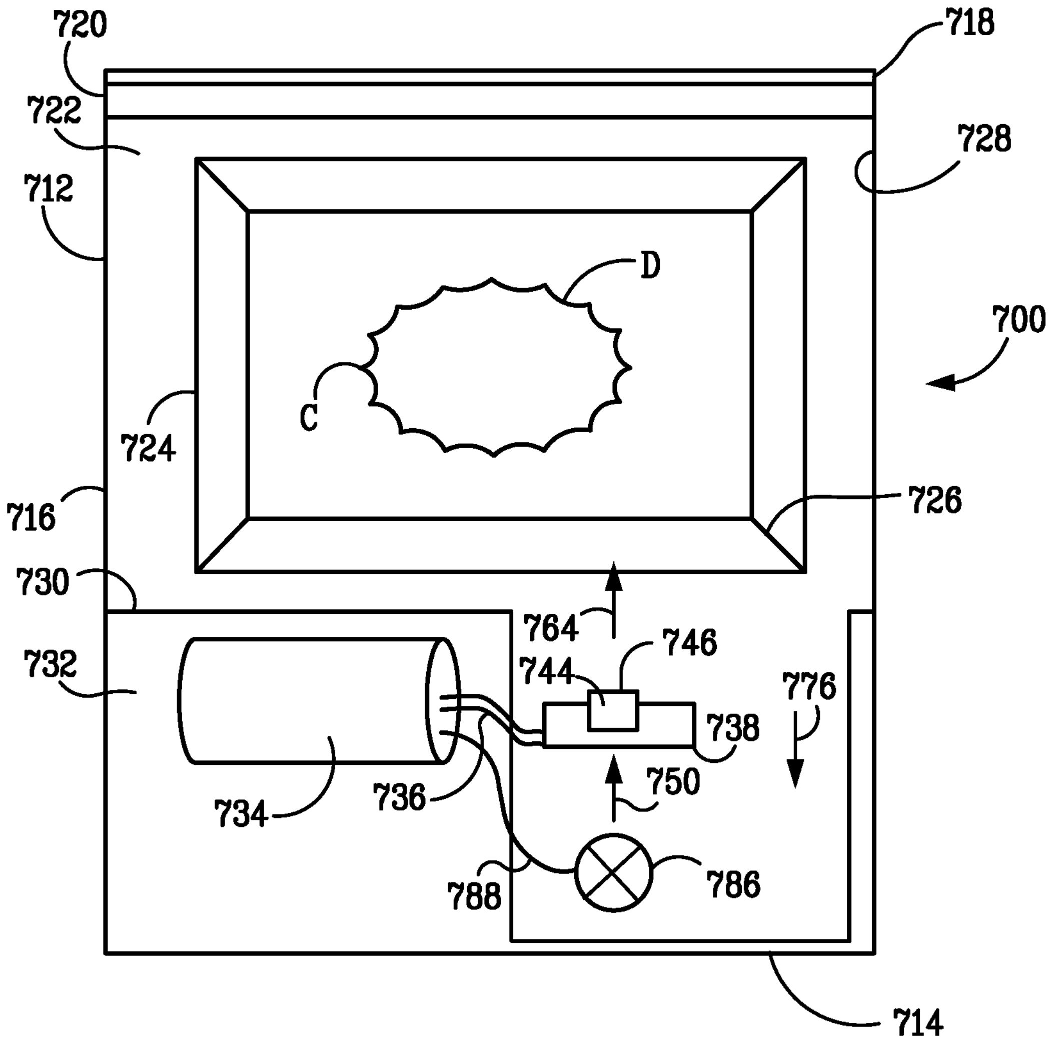
FIG. 8 presents a schematic view of another form of a disposable operating room coating applicator container 700, in accordance herewith.

Referring now to FIG. 8 a schematic view of another form of a disposable operating room coating applicator container 700, in accordance herewith, is presented. Disposable coating applicator container 700 of FIG. 8 is designed to apply a coating of a therapeutic agent C upon an object D to be coated. The disposable coating applicator container 700 includes a sealable container 712, the sealable container 712 having a container bottom 714, the container bottom 714 having upwardly extending walls 716, each upwardly extending wall 716 terminating in an upper edge 718.

Sealable container 712 also includes a closure 720 for sealing a device compartment 722. The device compartment 722 is formed by the upwardly extending walls 716, the closure 720, located adjacent to the upper edges 718 of the upwardly extending walls 716, and a device compartment floor 730. The closure 720 may be in the form of a zip-lock closure, a rib and groove-type closure, or the like, providing a reliable and full closure of the sealable container 712. The disposable coating applicator container 700 comprises a flexible material, such as a polymeric material, or multilayer polymeric composite, and may be in the form of a bag-like structure, as shown.

As with the forms of FIGS. 1-7, device compartment 122 is sized to allow the positioning of object D, which again may be an implant or the like, inside the device compartment 722 of sealable container 712. An optional spacer 724, which can be in the form of a wire frame 726, may be positioned in device compartment 722 to ensure adequate gas space around object D. Spacer 724 serves to enable gas or vapor flow inside device compartment 722, making the surfaces or at least a majority of the surfaces of object D accessible to gas or vapor flowing inside device compartment 722 and preventing at least some or most of the surfaces of object D, from touching the inner walls 728 of device compartment 722 and/or from being occluded by the inner walls 728 of device compartment 722.

Disposable operating room coating applicator container 700 also includes a bottom section 732, which may be positioned opposite closure 720. In other forms, bottom section 720 can be positioned on any side of disposable operating room coating applicator container 700. Bottom section 732 may be configured to be generally separated from device compartment 722.

As shown, bottom section 732 contains a power supply or battery 734 that is connected by electric leads or traces 736 to a heat source 738, the heat source 738 positioned within the device compartment 722. In some forms, the heat source 738 is a resistance heating element 738. An electric switch may be provided (not shown), so that by activating the switch, electric power from battery 734 is supplied to heating element 738 to initiate heating.

Still referring to FIG. 8, a subcompartment 740 is provided that is open directly into device compartment 722, with the source of therapeutic agent 744 positioned therein. In one form, heating element 734 is positioned in direct contact with therapeutic agent 744. As may be appreciated, gas or vapor can move from subcompartment 740 to apply a coating C to object D. Therapeutic agent 744 may be selected from anti-microbial agents, anti-bacterial agents, anti-viral agents, antibiotics, sanitizing agents, or combinations thereof.

In some forms, the therapeutic agent 744 is entrained in a carrier 746. In one form, the therapeutic agent 744 comprises triclosan and is supported on a carrier 746 in the form of an inert patch, such as a porous or absorbent patch, which can be made of any suitable polymer, or natural material, such as non-porous or porous paper, polyethylene, polypropylene, or the like. In some forms, the carrier 746 is positioned adjacent the resistance heating element 738. Alternatively, the therapeutic agent 744 can be deposited directly onto the heating element 738.

In one form, heating element 738 is positioned so as to be in direct contact with therapeutic agent 744. In some forms, the therapeutic agent 744 comprises triclosan and the carrier 746 comprises a sheet, pad or film comprising an absorbable polymer or silicone. In some forms, the absorbable polymer is lactide glycolide copolymer.

As shown in FIG. 8, a recirculating fan 786 is provided to facilitate the movement of gas and therapeutic agent 744. The recirculating fan 786 can be powered by power supply 734 via electric leads or traces 788. The recirculating fan 786 can be microprocessor (not shown) controlled to turn on or off as required and work in collaboration with the resistance heating element 738, which can also be microprocessor controlled, such as through a relay or logic-level Mosfet.

In some forms, a micro-light bulb, such as an LED bulb (not shown), can be installed in the electric circuit and configured to light up when electric power from battery 734 is supplied to heating element 738, providing indication to a user that disposable operating room coating applicator container 700 is operating normally. In some forms, a temperature indicating strip, such as a color-changing temperature indicator (not shown), can also be installed proximal to heating element 738, providing indication to a user that the heating element 738 is hot and that the system is operating normally.

In operation of disposable operating room coating applicator container 700, an object D is positioned inside device compartment 722, and closure 720 is closed. Power supply 734 is then switched on to supply power to heating element 738, which then heats up and increases the temperature of therapeutic agent 744. Recirculating fan 786 is powered-up to facilitate the movement of gas and therapeutic agent 744, as depicted by arrows 750, 760 and 776. Therapeutic agent 744 then evaporates or sublimates and is supplied into device compartment 722, where therapeutic agent 744 redeposits or forms a coating C on the surface of object D.

After sufficient time, such as 1, 3, 5, 10, 20, 60, 120, or 240 min, the power supply 734 is switched off or runs out of power. Closure 720 can be opened (or alternatively sealable container 712 cut open) and the coated object D then removed and used in a surgical procedure.

Advantageously, evaporating or sublimating therapeutic agent 744 is fully contained within disposable operating room coating applicator container 700.

Figure 9:
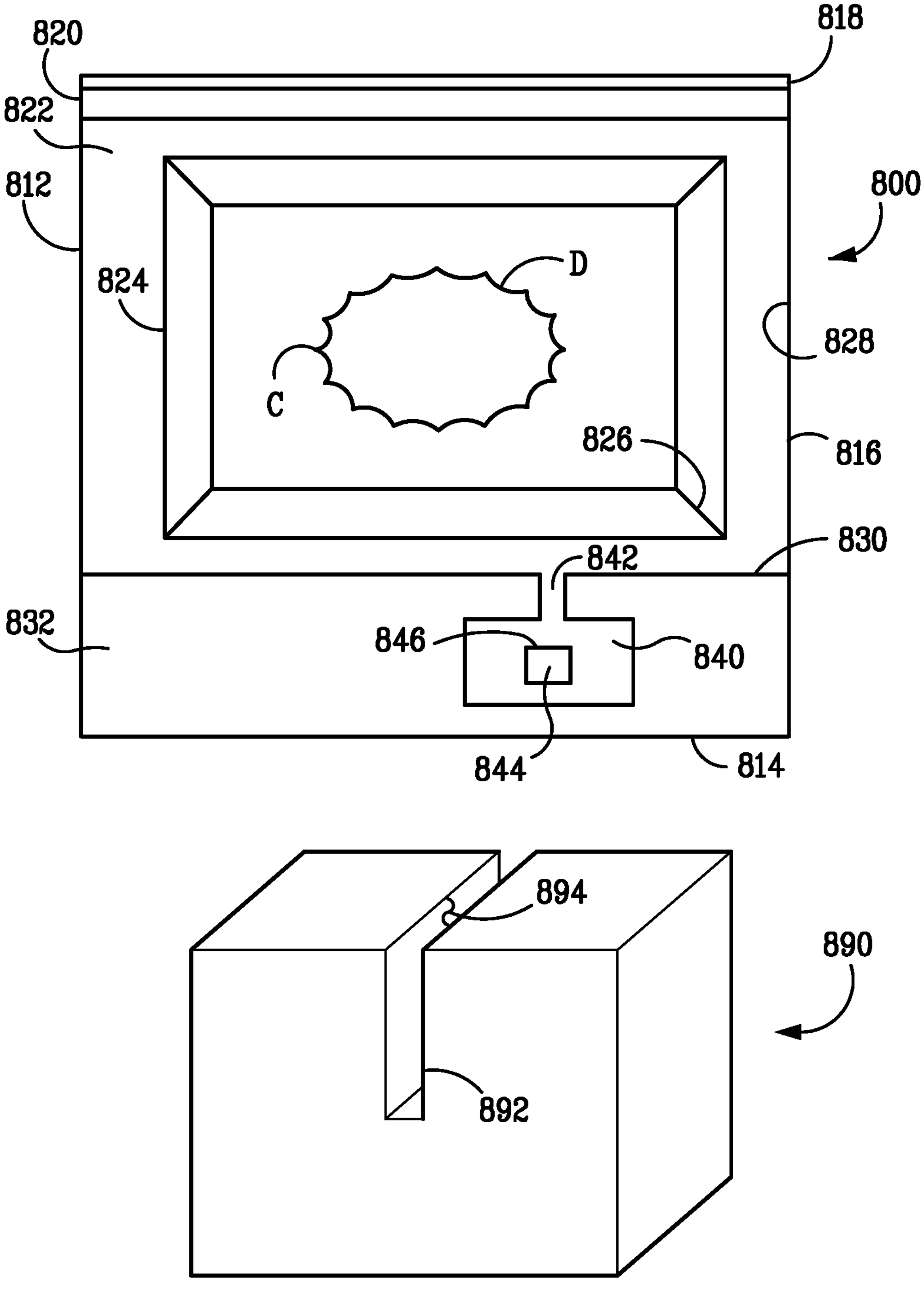
FIG. 9 presents a schematic view of yet another form of a disposable operating room coating applicator container 800, in accordance herewith.

Referring now to FIG. 9, a schematic view of one form of a disposable operating room coating applicator container 800, in accordance herewith, is presented. As presently conceived and intended to be practiced, disposable coating applicator container 800 of FIG. 9 is structured and arranged to apply a coating of a therapeutic agent C upon an object D to be coated. The disposable coating applicator container 800 includes a sealable container 812, the sealable container 812 having a container bottom 814, the container bottom 814 having upwardly extending walls 816, each upwardly extending wall 816 terminating in an upper edge 818.

Sealable container 812 also includes a closure 820 for sealing a device compartment 822. The device compartment 822 is formed by the upwardly extending walls 816, the closure 820, located adjacent to the upper edges 818 of the upwardly extending walls 816, and a device compartment floor 830. The closure 820 may be in the form of a zip-lock closure, a rib and groove-type closure, or the like, providing a reliable and full closure of the sealable container 812. The disposable coating applicator container 800 comprises a flexible material, such as a polymeric material, or multilayer polymeric composite, and may be in the form of a bag-like structure, as shown.

The device compartment 822 is sized to allow the positioning of object D, which may be an implant or the like, inside the device compartment 822 of sealable container 812. An optional spacer 824, which can be in the form of a wire frame 826, may be positioned in device compartment 822 to ensure adequate gas space around object D. As may be appreciated by those skilled in the art, spacer 824 serves to enable gas or vapor flow inside device compartment 822, making the surfaces or at least a majority of the surfaces of object D accessible to gas or vapor flowing inside device compartment 822 and preventing at least some or most of the surfaces of object D, from touching the inner walls 828 of device compartment 822 and/or from being occluded by the inner walls 828 of device compartment 822.

Disposable operating room coating applicator container 800 also includes a bottom section 832, which may be positioned opposite closure 820. As will be appreciated by those skilled in the art, in other forms, bottom section 820 can be positioned on any side of disposable operating room coating applicator container 800. Bottom section 832 may be configured to be generally separated from device compartment 822.

A separate power unit 890 having either a battery driven power supply (not shown), or energized by connecting to a standard AC or DC power supply (not shown), is structured, arranged and configured to accept at least a portion of the bottom section 820 of disposable coating applicator container 800 into a slit 892. Slit 892 is sized to allow insertion, removal and a snug fit of bottom section 820 within slit 892. The inside surface 894 of slit 892 is configured to be electrically heated, at least in the areas aligned with subcompartment 840.

The battery driven power supply or AC or DC power supply of separate power unit 890 may be connected by electric leads or traces to a heat source. In some forms, the heat source is a resistance heating element. An electric switch may be provided (not shown), so that by activating the switch, electric power from the battery driven power supply or AC or DC power supply of separate power unit 890 is supplied to the heating element to initiate heating.

Within the bottom section 832 there is a subcompartment 840 that is connected by a passage or channel 842 that is in fluid communication with device compartment 822, so that gas or vapor can move from subcompartment 840 to device compartment 822 via channel 842.

Referring again to FIG. 9, positioned within subcompartment 840 is a source of evaporable or sublimable medicant or therapeutic agent 844, useful for applying a coating C on object D. Therapeutic agent 844 may be selected from anti-microbial agents, anti-bacterial agents, anti-viral agents, antibiotics, sanitizing agents, or combinations thereof.

In some forms, the therapeutic agent 844 is entrained in a carrier 846. In one form, the therapeutic agent 844 comprises triclosan and is supported on a carrier 46 in the form of an inert patch, such as a porous or absorbent patch, which can be made of any suitable polymer, or natural material, such as non-porous or porous paper, polyethylene, polypropylene, or the like. In some forms, the carrier 846 is positioned adjacent the resistance heating element 838.

As indicated, when bottom section 832 is positioned within slot 892 of separate power unit 890, the heating element of power unit 890 is positioned so as to be in close proximity of, or adjacent to, therapeutic agent 844. In some forms, the therapeutic agent 844 comprises triclosan and the carrier 846 comprises a sheet, pad or film comprising an absorbable polymer or silicone. In some forms, the absorbable polymer is lactide glycolide copolymer.

In some forms, a micro-light bulb, such as an LED bulb (not shown), can be installed in the electric circuit of separate power unit 890 and configured to light up when electric power from battery driven power supply or the AC or DC power supply of separate power unit 890 is supplied to the heating element of separate power unit 890, providing indication to a user that disposable operating room coating applicator container 800 is operating normally. In some forms, a temperature indicating strip, such as a color-changing temperature indicator (not shown), can also be installed proximal to the heating element of separate power unit 890, providing indication to a user that the heating element is hot, and that the system is operating normally.

In operation of disposable operating room coating applicator container 800, an object D is positioned inside device compartment 22, and closure 820 is closed. The battery driven power supply or AC or DC power supply of separate power unit 890 is then switched on to supply power to heating element of separate power unit 890, which then heats up and increases the temperature of therapeutic agent 484 inside subcompartment 840. Therapeutic agent 844 then evaporates or sublimates and is supplied via channel 842 into device compartment 822, where therapeutic agent 844 redeposits or forms a coating C on the surface of object D.

After sufficient time, such as 1, 3, 5, 10, 20, 60, 120, or 240 min, the battery driven power supply or AC or DC power supply of separate power unit 890 is switched off or runs out of power. Closure 820 can be opened (or alternatively sealable container 812 cut open) and the coated object D then removed and used in a surgical procedure.

Advantageously, evaporating or sublimating therapeutic agent 844 is fully contained within disposable operating room coating applicator container 800. Advantageously, only a small portion of disposable operating room coating applicator container 800 is heated, namely subcompartment 840.

Similar to the above described embodiments, according to a further form, disposable operating room coating applicator container 800 may also include a vapor circulating pump (not shown), such as compressible elastic bulb or bellows, connected to disposable operating room coating applicator container 800 and/or gas circulating pump, such as a compressible elastic bulb or bellows, connected to disposable operating room coating applicator container 800, as has been described for the forms depicted in FIGS. 4-7. A separate power unit may also be provided and is configured for accepting bottom section 832 of disposable operating room coating applicator container 800 into a slit 892 of separate power unit 890. The vapor circulating pump 60 and/or gas circulating pump may be actuated by power unit 890 or manually, as described hereinabove.

Figure 10:
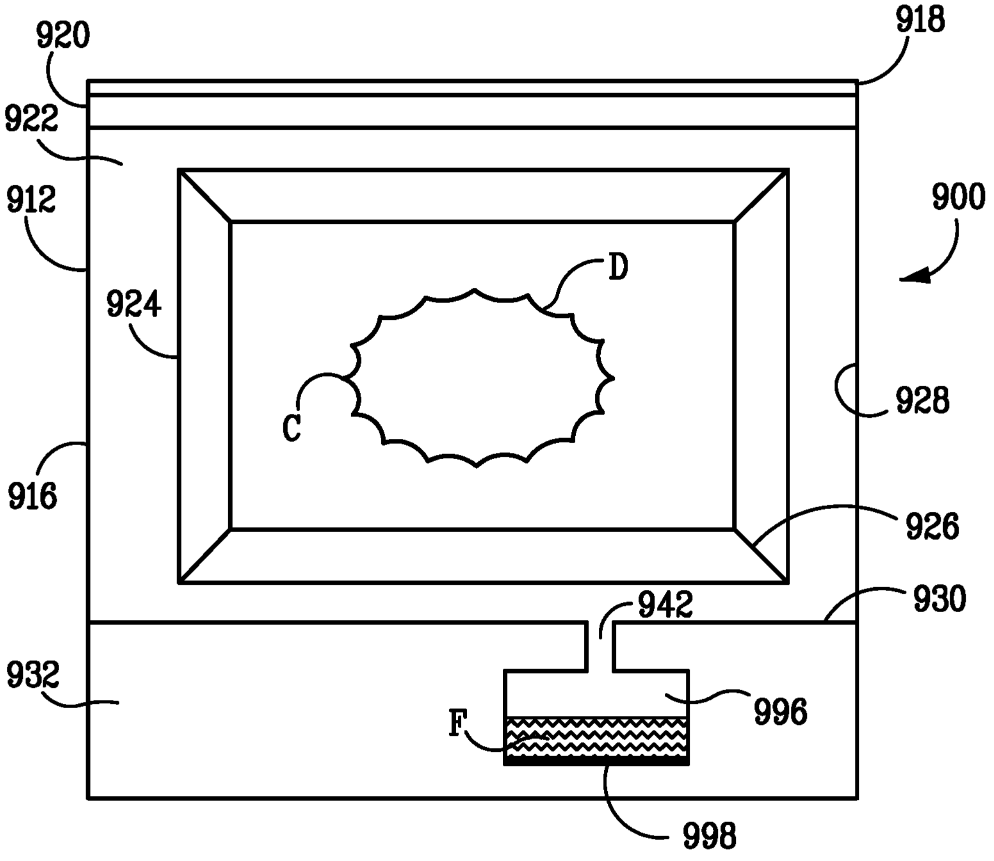
FIG. 10 presents a schematic view of still yet another form of a disposable operating room coating applicator container 900, in accordance herewith.

Referring now to FIG. 10, a schematic view of one form of a disposable operating room coating applicator container 800, in accordance herewith, is presented. As presently conceived and intended to be practiced, disposable coating applicator container 800 of FIG. 9 is structured and arranged to apply a coating of a therapeutic agent C upon an object D to be coated. The disposable coating applicator container 800 includes a sealable container 812, the sealable container 812 having a container bottom 814, the container bottom 184 having upwardly extending walls 816, each upwardly extending wall 16 terminating in an upper edge 818.

Sealable container 812 also includes a closure 820 for sealing a device compartment 822. The device compartment 822 is formed by the upwardly extending walls 816, the closure 820, located adjacent to the upper edges 818 of the upwardly extending walls 816, and a device compartment floor 830. The closure 820 may be in the form of a zip-lock closure, a rib and groove-type closure, or the like, providing a reliable and full closure of the sealable container 812. The disposable coating applicator container 800 comprises a flexible material, such as a polymeric material, or multilayer polymeric composite, and may be in the form of a bag-like structure, as shown.

The device compartment 822 is sized to allow the positioning of object D, which may be an implant or the like, inside the device compartment 822 of sealable container 812. An optional spacer 824, which can be in the form of a wire frame 826, may be positioned in device compartment 822 to ensure adequate gas space around object D. As may be appreciated by those skilled in the art, spacer 24 serves to enable gas or vapor flow inside device compartment 822, making the surfaces or at least a majority of the surfaces of object D accessible to gas or vapor flowing inside device compartment 822 and preventing at least some or most of the surfaces of object D, from touching the inner walls 828 of device compartment 22 and/or from being occluded by the inner walls 828 of device compartment 822.

Disposable operating room coating applicator container 810 also includes a bottom section 832, which may be positioned opposite closure 820. As will be appreciated by those skilled in the art, in other forms, bottom section 820 can be positioned on any side of disposable operating room coating applicator container 800. Bottom section 832 may be configured to be generally separated from device compartment 822.

A separate power unit 890 having either a battery driven power supply (not shown), or energized by connecting to a standard AC or DC power supply (not shown), is structured, arranged and configured to accept at least a portion of the bottom section 820 of disposable coating applicator container 800 into a slit 892. Slit 892 is sized to allow insertion, removal and a snug fit of bottom section 820 within slit 892. The inside surface 894 of slit 892 is configured to be electrically heated, at least in the areas aligned with subcompartment 840.

The battery driven power supply or AC or DC power supply of separate power unit 890 may be connected by electric leads or traces to a heat source. In some forms, the heat source is a resistance heating element. An electric switch may be provided (not shown), so that by activating the switch, electric power from the battery driven power supply or AC or DC power supply of separate power unit 890 is supplied to the heating element to initiate heating.

Within the bottom section 832 there is a subcompartment 840 that is connected by a passage or channel 842 that is in fluid communication with device compartment 822, so that gas or vapor can move from subcompartment 840 to device compartment 822 via channel 842.

Referring again to FIG. 9, positioned within subcompartment 840 is a source of evaporable or sublimable medicant or therapeutic agent 844, useful for applying a coating C on object D. Therapeutic agent 844 may be selected from anti-microbial agents, anti-bacterial agents, anti-viral agents, antibiotics, sanitizing agents, or combinations thereof.

In some forms, the therapeutic agent 844 is entrained in a carrier 846. In one form, the therapeutic agent 844 comprises triclosan and is supported on a carrier 46 in the form of an inert patch, such as a porous or absorbent patch, which can be made of any suitable polymer, or natural material, such as non-porous or porous paper, polyethylene, polypropylene, or the like. In some forms, the carrier 846 is positioned adjacent the resistance heating element 838.

As indicated, when bottom section 832 is positioned within slot 892 of separate power unit 890, the heating element of power unit 890 is positioned so as to be in close proximity of, or adjacent to, therapeutic agent 844. In some forms, the therapeutic agent 844 comprises triclosan and the carrier 846 comprises a sheet, pad or film comprising an absorbable polymer or silicone. In some forms, the absorbable polymer is lactide glycolide copolymer.

In some forms, a micro-light bulb, such as an LED bulb (not shown), can be installed in the electric circuit of separate power unit 890 and configured to light up when electric power from battery driven power supply or the AC or DC power supply of separate power unit 890 is supplied to the heating element of separate power unit 890, providing indication to a user that disposable operating room coating applicator container 800 is operating normally. In some forms, a temperature indicating strip, such as a color-changing temperature indicator (not shown), can also be installed proximal to the heating element of separate power unit 890, providing indication to a user that the heating element is hot, and that the system is operating normally.

In operation of disposable operating room coating applicator container 800, an object D is positioned inside device compartment 822, and closure 820 is closed. The battery driven power supply or AC or DC power supply of separate power unit 890 is then switched on to supply power to heating element of separate power unit 890, which then heats up and increases the temperature of therapeutic agent 844 inside subcompartment 840. Therapeutic agent 844 then evaporates or sublimates and is supplied via channel 842 into device compartment 822, where therapeutic agent 844 redeposits or forms a coating C on the surface of object D.

After sufficient time, such as 1, 3, 5, 10, 20, 60, 120, or 240 min, the battery driven power supply or AC or DC power supply of separate power unit 890 is switched off or runs out of power. Closure 820 can be opened (or alternatively sealable container 812 cut open) and the coated object D then removed and used in a surgical procedure.

Advantageously, evaporating or sublimating therapeutic agent 844 is fully contained within disposable operating room coating applicator container 800. Advantageously, only a small portion of disposable operating room coating applicator container 800 is heated, namely subcompartment 840.

Similar to the above described embodiments, according to a further form, disposable operating room coating applicator container 800 may also include a vapor circulating pump (not shown), such as compressible elastic bulb or bellows, connected to disposable operating room coating applicator container 800 and/or gas circulating pump, such as a compressible elastic bulb or bellows, connected to disposable operating room coating applicator container 800, as has been described for the forms depicted in FIGS. 4-7. A separate power unit may also be provided and is configured for accepting bottom section 832 of disposable operating room coating applicator container 800 into a slit 892 of separate power unit 890. The vapor circulating pump and/or gas circulating pump may be actuated by power unit 890 or manually, as described hereinabove.

Referring now to FIG. 10, a schematic view of another form of a disposable operating room coating applicator container 900, in accordance herewith, is presented. As presently conceived and intended to be practiced, disposable coating applicator container 900 is structured and arranged to apply a coating of a therapeutic agent C upon an object D to be coated. The disposable coating applicator container 900 includes a sealable container 912, the sealable container 912 having a container bottom 914, the container bottom 984 having upwardly extending walls 916, each upwardly extending wall 916 terminating in an upper edge 918.

Sealable container 912 also includes a closure 920 for sealing a device compartment 922. The device compartment 922 is formed by the upwardly extending walls 916, the closure 920, located adjacent to the upper edges 918 of the upwardly extending walls 916, and a device compartment floor 930. The closure 920 may be in the form of a zip-lock closure, a rib and groove-type closure, or the like, providing a reliable and full closure of the sealable container 912. The disposable coating applicator container 900 comprises a flexible material, such as a polymeric material, or multilayer polymeric composite, and may be in the form of a bag-like structure, as shown.

The device compartment 922 is sized to allow the positioning of object D, which may be an implant or the like, inside the device compartment 922 of sealable container 912. An optional spacer 924, which can be in the form of a wire frame 926, may be positioned in device compartment 922 to ensure adequate gas space around object D. As may be appreciated by those skilled in the art, spacer 924 serves to enable gas or vapor flow inside device compartment 922, making the surfaces or at least a majority of the surfaces of object D accessible to gas or vapor flowing inside device compartment 922 and preventing at least some or most of the surfaces of object D, from touching the inner walls 928 of device compartment 922 and/or from being occluded by the inner walls 928 of device compartment 922.

Disposable operating room coating applicator container 900 also includes a bottom section 932, which may be positioned opposite closure 920. As will be appreciated by those skilled in the art, in other forms, bottom section 920 can be positioned on any side of disposable operating room coating applicator container 900. Bottom section 932 may be configured to be generally separated from device compartment 922.

Disposable operating room coating applicator container 900 also includes a fluid compartment 996 formed within section 932, that is in fluid communication with device compartment 922 via channel 942 and containing a fluid F such as an antibiotic solution. The fluid F can be nebulized into fine droplets or mist by contacting fluid compartment 996 with a vibratory actuator 998, such as am ultrasonic plate. Mist from fluid compartment 996 can then move into device compartment 922 via channel 942 and redeposit and/or coat on object D.

Fluid compartment 996 is configured to receive a quanta of therapeutic agent, in the form of Fluid F. In this and various other embodiments, the therapeutic agent may be in the form of an aqueous solution and/or an aqueous suspension of the therapeutic agent. The fluid compartment 996 may be fillable with a dispenser such as a syringe or an eyedropper or other suitable dispenser. It is also envisioned, that the fluid compartment 996 may be prefilled and provided with a breachable cover whereby the therapeutic agent may be retained in the fluid compartment 996 until use.

The vibratory actuator 998 at the bottom of fluid compartment 996 may be in the form of a commonplace ultrasonic nebulizer, such as a vibrating piezoelectric disk or plate, widely commercially available from suppliers worldwide such as AMAZON. It is envisioned that a number of different forms of atomizers may be used, such as by way of non-limiting examples, a jet nebulizer and/or a vibrating mesh nebulizer and/or a pressurized spray-nozzle nebulizer and/or a heated frit nebulizer and/or a heated wick aerosol generator and/or a heated capillary, among others. One common aspect that may be shared amongst devices being considered for use as an atomizer in accordance with this disclosure is a capability of the candidate atomizer to transform a solution or suspension of a therapeutic agent into mist, cloud vapor or aerosol comprising tiny liquid particles (tiny droplets) of a therapeutic agent that may remain suspended in air for a time sufficient to coat an object D in accordance with the teachings herein.

As may be appreciated, a separate power unit may be provided (not shown, but see FIG. 9, element 890 for details) to power vibratory actuator 998. The power unit may include a battery driven power supply, or it may energize vibratory actuator 998 by connecting it to a standard AC or DC power supply. Referring to FIG. 9, it may be structured, arranged and configured to accept at least a portion of the bottom section 920 of disposable coating applicator container 900 into a slit 892. Slit 892 is sized to allow insertion, removal and a snug fit of bottom section 820 within slit 892. The inside surface 894 of slit 892 may be configured to provide an electrical connection.

An electric switch may be provided (not shown), so that by activating the switch, electric power from the battery driven power supply or AC or DC power supply of separate a power unit may be supplied to the vibratory actuator 998.

In some forms, a micro-light bulb, such as an LED bulb (not shown), can be installed in the electric circuit of a separate power unit and configured to light up when electric power from battery driven power supply or the AC or DC power supply of a separate power unit is supplied to the vibratory actuator 998, providing indication to a user that disposable operating room coating applicator container 900 is operating normally.

In operation of disposable operating room coating applicator container 900, an object D is positioned inside device compartment 922, and closure 920 is closed. A battery driven power supply or an AC or DC power supply is then switched on to supply power to vibratory actuator 998, which then nebulizes a fluid F, which may be an antibiotic solution. Fluid F, which may be an antibiotic solution, is supplied via channel 942 into device compartment 996, where Fluid F, such as an antibiotic solution forms a coating C on the surface of object D.

After sufficient time, such as 1, 3, 5, 10, 20, 60, 120, or 240 min, the battery driven power supply or AC or DC power supply of separate power unit 990 is switched off or runs out of power. Closure 920 can be opened (or alternatively sealable container 912 cut open) and the coated object D then removed and used in a surgical procedure.

Advantageously, Fluid F, which may be an antibiotic solution is fully contained within disposable operating room coating applicator container 900.

According to a further form, disposable operating room coating applicator container 900 may also include a pump (not shown), such as a compressible elastic bulb or bellows, connected to disposable operating room coating applicator container 900. A separate power unit may also be provided and may be configured for accepting bottom section 932 of disposable operating room coating applicator container 900 into a slit 892 of separate power unit 890 (see FIG. 9). The pump may be actuated by power unit 890 or manually, as described hereinabove.

Figure 11:
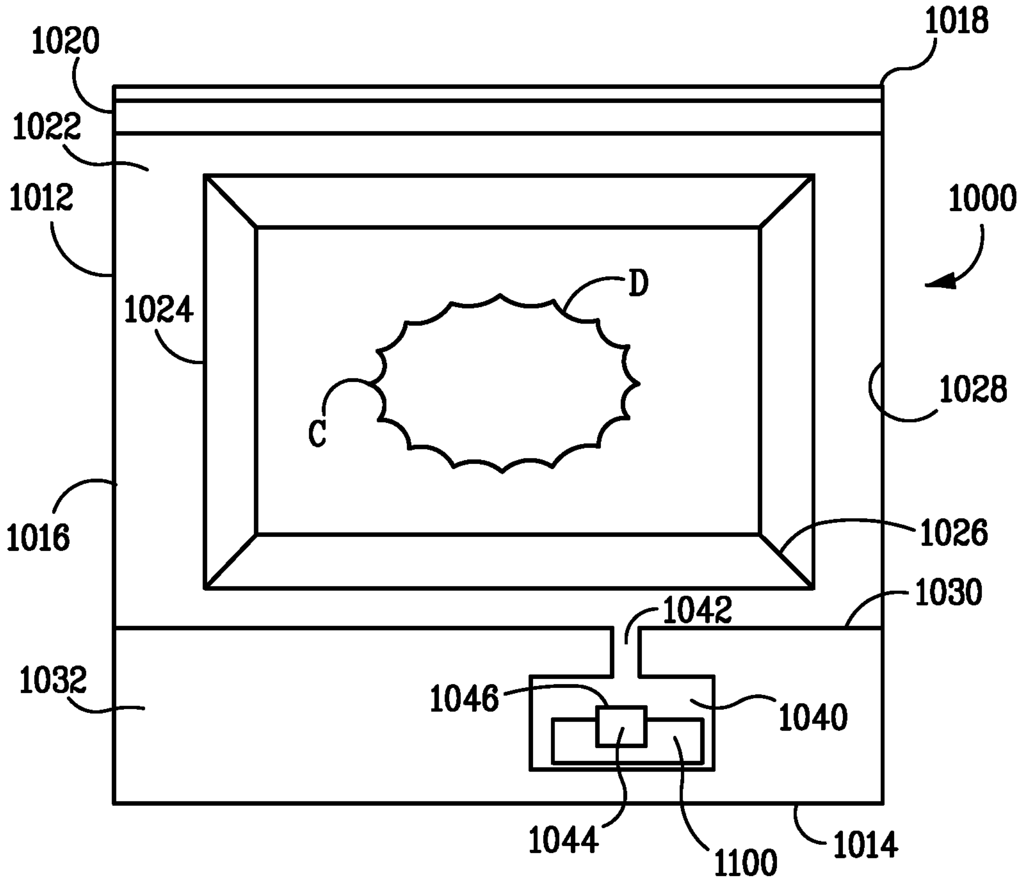
FIG. 11 presents a schematic view of another form of a disposable operating room coating applicator container 1000, in accordance herewith.

Referring now to FIG. 11, a schematic view of one form of a disposable operating room coating applicator container 1000, in accordance herewith, is presented. Disposable coating applicator container 1000 is structured and arranged to apply a coating of a therapeutic agent C upon an object D to be coated. The disposable coating applicator container 1000 includes a sealable container 1012, the sealable container 1012 having a container bottom 1014, the container bottom 1014 having upwardly extending walls 1016, each upwardly extending wall 16 terminating in an upper edge 1018.

Sealable container 1012 also includes a closure 1020 for sealing a device compartment 1022. The device compartment 1022 is formed by the upwardly extending walls 1016, the closure 1020, located adjacent to the upper edges 1018 of the upwardly extending walls 1016, and a device compartment floor 1030. The closure 1020 may be in the form of a zip-lock closure, a rib and groove-type closure, or the like, providing a reliable and full closure of the sealable container 1012. The disposable coating applicator container 1000 comprises a flexible material, such as a polymeric material, or multilayer polymeric composite, and may be in the form of a bag-like structure, as shown.

The device compartment 1022 is sized to allow the positioning of object D, which may be an implant or the like, inside the device compartment 1022 of sealable container 1012. An optional spacer 1024, which can be in the form of a wire frame 1026, may be positioned in device compartment 1022 to ensure adequate gas space around object D. As may be appreciated by those skilled in the art, spacer 1024 serves to enable gas or vapor flow inside device compartment 1022, making the surfaces or at least a majority of the surfaces of object D accessible to gas or vapor flowing inside device compartment 1022 and preventing at least some or most of the surfaces of object D, from touching the inner walls 1028 of device compartment 1022 and/or from being occluded by the inner walls 1028 of device compartment 1022.

Disposable operating room coating applicator container 1000 also includes a bottom section 1032, which may be positioned opposite closure 1020. As will be appreciated by those skilled in the art, in other forms, bottom section 1020 can be positioned on any side of disposable operating room coating applicator container 1000. Bottom section 1032 may be configured to be generally separated from device compartment 1022.

Within the bottom section 1032 there is a subcompartment 1040 that is connected by a passage or channel 1042 that is in fluid communication with device compartment 1022, so that gas or vapor can move from subcompartment 1040 to device compartment 1022 via channel 1042.

Referring again to FIG. 11, positioned within subcompartment 1040 is a source of evaporable or sublimable medicant or therapeutic agent 1044, useful for applying a coating C on object D. Therapeutic agent 1044 may be selected from anti-microbial agents, anti-bacterial agents, anti-viral agents, antibiotics, sanitizing agents, or combinations thereof.

In some forms, the therapeutic agent 1044 is entrained in a carrier 1046. In one form, the therapeutic agent 1044 comprises triclosan and is supported on a carrier 1046 in the form of an inert patch, such as a porous or absorbent patch, which can be made of any suitable polymer, or natural material, such as non-porous or porous paper, polyethylene, polypropylene, or the like. In some forms, the carrier 1046 is positioned adjacent the resistance heating element 1038.

In some forms, the therapeutic agent 1044 comprises triclosan and the carrier 1046 comprises a sheet, pad or film comprising an absorbable polymer or silicone. In some forms, the absorbable polymer is lactide glycolide copolymer.

As mentioned, inside subcompartment 1044 is positioned a source of evaporable or sublimable medicant 1044. In one form, a metallic element 1100 is positioned inside subcompartment 1044 or in immediate proximity to subcompartment 1044, or one form, in direct contact with therapeutic agent 1044.

Subcompartment 1044 is configured to be heated by any suitable external source of energy. In one form, subcompartment 1044 is heated by an induction heater (not shown), which then heats metallic element 1100. In one form, subcompartment 1044 is heated by microwave or radiofrequency energy. In another form, subcompartment 1044 is heated by immersion in a hot water bath, or any hot bath. In one form, subcompartment 1044 is heated by contact with a hot plate.

In some forms, a temperature indicating strip, such as a color-changing temperature indicator (not shown), can also be installed proximal to the subcompartment 1040, providing indication to a user that the that the system is operating normally.

In operation of disposable operating room coating applicator container 1000, an object D is positioned inside device compartment 1022, and closure 1020 is closed. Subcompartment 1040 is the heated by any of the above methods, which then increases the temperature of therapeutic agent 1044 inside subcompartment 1040. Therapeutic agent 1044 then evaporates or sublimates and is supplied via channel 1042 into device compartment 1022, where therapeutic agent 1044 redeposits or forms a coating C on the surface of object D.

After sufficient time, such as 1, 3, 5, 10, 20, 60, 120, or 240 min, the heating is continued. Closure 1020 can be opened (or alternatively sealable container 1012 cut open) and the coated object D then removed and used in a surgical procedure.

Advantageously, evaporating or sublimating therapeutic agent 844 is fully contained within disposable operating room coating applicator container 1000. Advantageously, only a small portion of disposable operating room coating applicator container 1000 is heated, namely subcompartment 1040.

Since the implant is in-part thermally insulated from the thermal source by a standoff mesh, and by virtue of the fact that the process occurs rapidly and the thermal mass of the implant is large with respect to the thermal mass of heating element, thermal equilibrium between the thermal source and the implant never occurs. Consequently, the implant is usually significantly cooler than the thermal source. The temperature difference (or thermal gradient) can be from about 50° C. to about 150° C. for a coating device designed to coat triclosan onto an implant or other medical device. As such, a very significant thermodynamic driving force for condensation of the hot vapor on the relatively cold surface of the implant is present. This helps to drive the condensation of the active agent onto a variety of different surfaces that the active agent would otherwise not preferably absorb onto. In this way the presently disclosed device and method differs significantly from previous processes used to make triclosan impregnated absorbable sutures, such as disclosed in US Published Patent Application 2004/0220614 to Scalzo, et. al.

In another aspect, provided is a method of coating an object with a therapeutic agent. The method includes the steps of placing an object to be coated into a disposable coating applicator container, the disposable coating applicator container comprising: a sealable container, the sealable container having a container bottom, the container bottom having upwardly extending walls, each upwardly extending wall terminating in an upper edge, and a closure for sealing a device compartment formed in part by the upwardly extending walls, the closure adjacent to the upper edges of the upwardly extending walls; and a therapeutic agent positioned in fluid communication with the device compartment; sealing the device compartment; dispersing a therapeutic agent within the sealed device compartment by atomizing the therapeutic agent; and coating the object with the therapeutic agent, wherein the disposable coating applicator container comprises a flexible material and is in the form of a bag-like structure.

In some forms, the method includes the step of removing the coated object from the device compartment.

In some forms, the therapeutic agent is entrained in a carrier. In some forms, the therapeutic agent comprises triclosan and the carrier comprises a sheet, pad or film comprising an absorbable polymer or silicone. In some forms, the absorbable polymer is lactide glycolide copolymer.

In some forms, the disposable coating applicator container further comprises a heat source for vaporizing the therapeutic agent and causing the therapeutic agent to flow into the device compartment and coat the object. In some forms, the heat source is a resistance heater. In some forms, the carrier is positioned adjacent the resistance heater. In some forms, the resistance heater is located within the disposable coating applicator container. In some forms, the resistance heater is located within the device compartment. In some forms, the resistance heater is located outside the disposable coating applicator container.

In some forms, the disposable coating applicator container further comprises a power supply for powering the resistance heater. In some forms, the power supply is located within the disposable coating applicator container. In some forms, the power supply is a battery. In some forms, the heat source is a chemical heat pack.

In some forms, the disposable coating applicator container further comprises a vapor circulating pump, the vapor circulating pump in fluid communication with the heated therapeutic agent entrained in the carrier. In some forms, the disposable coating applicator container further comprises a gas circulating pump, the gas circulating pump in fluid communication with the device compartment. In some forms, the vapor circulating pump and the gas circulating pump are hand-operated, bulb- or bellows-type pumps. In some forms, the disposable coating applicator container further comprises a gas circulating pump, the gas circulating pump in fluid communication with the device compartment.

In some forms, the disposable coating applicator container further comprises a recirculating pump, the recirculating pump in fluid communication with the heated therapeutic agent entrained in the carrier and the device compartment, and is configured to alternately apply pressure and vacuum via a check-valve system.

In some forms, the disposable coating applicator container further comprises a therapeutic agent supply cannula, in fluid communication with a first side of the device compartment and an intake cannula in fluid communication with a second side of the device compartment. In some forms, the therapeutic agent supply cannula and the intake cannula each have a plurality of apertures spaced thereabout to more evenly provide the therapeutic agent and more evenly draw return intake gas.

In some forms, the disposable coating applicator container further comprises a recirculating fan, powered by the power supply, to facilitate the provision of therapeutic agent and the return of intake gas. In some forms, the disposable coating applicator container further comprises a microprocessor for controlling the recirculating fan.

In some forms, the disposable coating applicator container further comprises an external power block, the external power block having a slit for positioning the disposable coating applicator container therein, and applying heat to the therapeutic agent entrained within the carrier.

In some forms, the therapeutic agent comprises a fluid and the disposable coating applicator container further comprises an atomizer operable to atomize the therapeutic agent. In some forms, the atomizer comprises a nebulizer. In some forms, the atomizer comprises an ultrasonic nebulizer and/or a jet nebulizer and/or a vibrating mesh nebulizer and/or a pressurized spray nozzle nebulizer and/or a vibrated frit nebulizer and/or a thermally driven, wick-based aerosol generator and/or a heated capillary aerosol generator and/or a vaporizer. In some forms, the therapeutic agent comprises a suspension and/or an emulsion and/or a solution.

In some forms, a source of vacuum is applied to the device compartment.

In some forms, the heat source is an external induction or hot water heat source. In some forms, the heat source is a metallic element positioned adjacent the therapeutic agent. In some forms, the heat source comprises an external source of energy.

In some forms, the object is a surgical implant and/or a medical device.

In some forms, the flexible material comprises a polymer, copolymer or blends thereof.

Additionally, the method can further comprise contacting the medical device with the vaporized therapeutic agent while the vaporized therapeutic agent is in a heated condition. During the contacting, the temperature of the medical device increases by less than 15° C.

INDUSTRIAL APPLICABILITY

The systems and methods disclosed herein are applicable to the medical device industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and sub-combinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and sub-combinations that are directed to one of the disclosed inventions and are novel and non-obvious. Inventions embodied in other combinations and sub-combinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

While the present disclosure is being illustrated and described below by reference to particular forms, those of ordinary skill in the art will appreciate that the invention lends itself to variations not necessarily illustrated herein. For this reason, then, reference should be made solely to the appended claims for purposes of determining the true scope of the present disclosure.

What is claimed is:

1. A disposable coating applicator container for applying a coating of a therapeutic agent upon an object to be coated, comprising:

a sealable container, the sealable container having a container bottom, the container bottom having upwardly extending walls, each upwardly extending wall terminating in an upper edge, and a closure for sealing a device compartment formed in part by the upwardly extending walls, the closure adjacent to the upper edges of the upwardly extending walls;

a therapeutic agent positioned in fluid communication with the device compartment, wherein the disposable coating applicator container comprises a flexible material and is in the form of a bag structure; and a heat source for vaporizing the therapeutic agent and causing the therapeutic agent to flow into the device compartment and coat the object, wherein the heat source is disposed within the disposable coating applicator container.

2. The disposable coating applicator container of claim 1, wherein the therapeutic agent is entrained in a carrier.

3. The disposable coating applicator container of claim 2, wherein the therapeutic agent comprises triclosan and the carrier comprises a sheet, pad or film comprising an absorbable polymer or silicone.

4. The disposable coating applicator container of claim 3, wherein the absorbable polymer is lactide glycolide copolymer.

5. The disposable coating applicator container of claim 1, wherein the heat source is a resistance heater.

6. The disposable coating applicator container of claim 5, wherein the carrier is positioned adjacent the resistance heater.

7. The disposable coating applicator container of claim 6, wherein the resistance heater is located within the device compartment.

8. The disposable coating applicator container of claim 6, wherein the resistance heater is located outside the disposable coating applicator container.

9. The disposable coating applicator container of claim 5, further comprising a power supply for powering the resistance heater.

10. The disposable coating applicator container of claim 9, wherein the power supply is located within the disposable coating applicator container.

11. The disposable coating applicator container of claim 10, wherein the power supply is a battery.

12. The disposable coating applicator container of claim 9, further comprising a recirculating fan, powered by the power supply, to facilitate the provision of therapeutic agent and the return of intake gas.

13. The disposable coating applicator container of claim 12, further comprising a microprocessor for controlling the recirculating fan.

14. The disposable coating applicator container of claim 5, further comprising a vapor circulating pump, the vapor circulating pump in fluid communication with the heated therapeutic agent entrained in the carrier.

15. The disposable coating applicator container of claim 14, further comprising a gas circulating pump, the gas circulating pump in fluid communication with the device compartment.

16. The disposable coating applicator container of claim 15, wherein the vapor circulating pump and the gas circulating pump are hand-operated, bulb- or bellows-type pumps.

17. The disposable coating applicator container of claim 5, further comprising a gas circulating pump, the gas circulating pump in fluid communication with the device compartment.

18. The disposable coating applicator container of claim 5, further comprising a recirculating pump, the recirculating pump in fluid communication with the heated therapeutic agent entrained in the carrier and the device compartment, and is configured to alternately apply pressure and vacuum via a check-valve system.

19. The disposable coating applicator container of claim 5, further comprising a therapeutic agent supply cannula, in fluid communication with a first side of the device compartment and an intake cannula in fluid communication with a second side of the device compartment.

20. The disposable coating applicator container of claim 19, wherein the therapeutic agent supply cannula and the intake cannula each have a plurality of apertures spaced thereabout to more evenly provide the therapeutic agent and more evenly draw return intake gas.

21. The disposable coating applicator container of claim 5, further comprising an external power block, the external power block having a slit for positioning the disposable coating applicator container therein, and applying heat to the therapeutic agent entrained within the carrier.

22. The disposable coating applicator container of claim 1, wherein the heat source is a chemical heat pack.

23. The disposable coating applicator container of claim 1, wherein the heat source is an external induction or hot water heat source.

24. The disposable coating applicator container of claim 23, wherein the heat source is a metallic element positioned adjacent the therapeutic agent.

25. The disposable coating applicator container of claim 24, wherein the heat source comprises an external source of energy.

26. The disposable coating applicator container of claim 25, wherein the heat source comprises a system employing microwave or radiofrequency energy.

27. The disposable coating applicator container of claim 1, wherein the object is a surgical implant and/or a medical device.

28. The disposable coating applicator container of claim 1, wherein the flexible material comprises a polymer, copolymer or blends thereof.

29. A disposable coating applicator container for applying a coating of a therapeutic agent upon an object to be coated, comprising:

a sealable container, the sealable container having a container bottom, the container bottom having upwardly extending walls, each upwardly extending wall terminating in an upper edge, and a closure for sealing a device compartment formed in part by the upwardly extending walls, the closure adjacent to the upper edges of the upwardly extending walls; and a therapeutic agent positioned in fluid communication with the device compartment, wherein the disposable coating applicator container comprises a flexible material and is in the form of a bag structure, wherein the therapeutic agent comprises a fluid and the disposable coating applicator container further comprises an atomizer operable to atomize the therapeutic agent.

30. The disposable coating applicator container of claim 29, wherein the atomizer comprises a nebulizer.

31. The disposable coating applicator container of claim 29, wherein the atomizer comprises an ultrasonic nebulizer and/or a jet nebulizer and/or a vibrating mesh nebulizer and/or a pressurized spray nozzle nebulizer and/or a vibrated frit nebulizer and/or a thermally driven, wick-based aerosol generator and/or a heated capillary aerosol generator and/or a vaporizer.

32. The disposable coating applicator container of claim 29, wherein the therapeutic agent comprises a suspension and/or an emulsion and/or a solution.

33. The disposable coating applicator container of claim 29, wherein a source of vacuum is applied to the device compartment.

* * * * *